US011813148B2

(12) United States Patent
Aviles et al.

(10) Patent No.: US 11,813,148 B2
(45) Date of Patent: Nov. 14, 2023

(54) WEBS WITH COMPOSITIONS APPLIED THERETO

(71) Applicant: The Procter & Gamble Company, Cincinnati, OH (US)

(72) Inventors: Misael Omar Aviles, Hamilton, OH (US); Martin Ian James, Hamilton, OH (US); Chad M. Weldishofer, Cincinnati, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 1063 days.

(21) Appl. No.: 16/529,819

(22) Filed: Aug. 2, 2019

(65) Prior Publication Data
US 2020/0038262 A1 Feb. 6, 2020

Related U.S. Application Data

(60) Provisional application No. 62/714,107, filed on Aug. 3, 2018.

(51) Int. Cl.
*A61F 13/15* (2006.01)
*A61F 13/511* (2006.01)
(Continued)

(52) U.S. Cl.
CPC .. *A61F 13/51121* (2013.01); *A61F 13/15699* (2013.01); *A61F 13/52* (2013.01);
(Continued)

(58) Field of Classification Search
CPC ................ A61F 13/51121; A61F 13/52; A61F 13/5616; A61F 13/565; A61F 2013/51014; A61F 2013/51028; A61F 2013/51033
See application file for complete search history.

(56) References Cited

U.S. PATENT DOCUMENTS 1,668,322 A 5/1928 Kessler, Jr.
1,867,314 A 7/1932 Gurwick
(Continued)

FOREIGN PATENT DOCUMENTS

CN 1286605 A 3/2001
CN 104323884 A 2/2015
(Continued)

OTHER PUBLICATIONS

International Search Report and Written Opinion for PCT/US2016/059242 dated Feb. 15, 2017.
(Continued)

*Primary Examiner* — Jacqueline F Stephens
(74) *Attorney, Agent, or Firm* — Amanda Herman Berghauer

(57) ABSTRACT

An absorbent article having a longitudinal centerline, a lateral centerline, a machine direction (MD) generally oriented parallel to the longitudinal centerline and a cross direction (CD) generally oriented parallel to the lateral centerline is described. The absorbent article includes a topsheet, a backsheet, and an absorbent core disposed therebetween. A plurality of composition elements is disposed on the topsheet, wherein each of the composition elements comprise an element width and an element spacing between adjacent elements, and wherein a ratio of element spacing to element width is between about 0.5 to about 8, as measured by the Composition Pattern Analysis.

19 Claims, 17 Drawing Sheets

(51) Int. Cl.
  *A61F 13/51* (2006.01)
  *A61F 13/56* (2006.01)
(52) U.S. Cl.
  CPC ........ *A61F 13/565* (2013.01); *A61F 13/5616* (2013.01); *A61F 2013/51014* (2013.01); *A61F 2013/51028* (2013.01); *A61F 2013/51033* (2013.01)

(56) References Cited

U.S. PATENT DOCUMENTS

| | | |
|---|---|---|
| 2,226,163 A | 12/1940 | Dufour |
| 2,427,765 A | 9/1947 | Chollar |
| 2,468,400 A | 4/1949 | Huebner |
| 2,864,310 A | 12/1958 | Nelson |
| 3,055,296 A | 9/1962 | Farrow |
| 3,056,384 A | 10/1962 | Beale et al. |
| 3,265,500 A | 8/1966 | Lewis |
| 3,294,016 A | 12/1966 | Kessler et al. |
| 3,301,746 A | 1/1967 | Sanford et al. |
| 3,473,576 A | 10/1969 | Amneus |
| 3,573,164 A | 3/1971 | Friedberg et al. |
| 3,738,269 A | 6/1973 | Wagner |
| 3,759,261 A | 9/1973 | Wang |
| 3,821,068 A | 6/1974 | Shaw |
| 3,896,722 A | 7/1975 | Farrow |
| 3,896,723 A | 7/1975 | Farrow et al. |
| 3,974,025 A | 8/1976 | Ayers |
| 3,994,771 A | 11/1976 | Morgan, Jr. et al. |
| 4,033,258 A | 7/1977 | Farrow |
| 4,041,951 A | 8/1977 | Sanford |
| 4,098,630 A | 7/1978 | Morse |
| 4,191,609 A | 3/1980 | Trokhan |
| 4,191,756 A | 3/1980 | Masi et al. |
| 4,231,370 A | 11/1980 | Mroz et al. |
| 4,239,065 A | 12/1980 | Trokhan |
| 4,243,446 A | 1/1981 | Mathey |
| 4,275,105 A | 6/1981 | Boyd et al. |
| 4,300,981 A | 11/1981 | Carstens |
| 4,333,979 A | 6/1982 | Sciaraffa et al. |
| 4,355,066 A | 10/1982 | Newman |
| 4,361,089 A | 11/1982 | Wittkopf et al. |
| 4,437,408 A | 3/1984 | Arkans |
| 4,440,597 A | 4/1984 | Wells et al. |
| 4,452,141 A | 6/1984 | Mistyurik |
| 4,458,399 A | 7/1984 | Kessler |
| 4,483,053 A | 11/1984 | Hamisch, Jr. |
| 4,526,098 A | 7/1985 | Bachman |
| 4,528,239 A | 7/1985 | Trokhan |
| 4,529,480 A | 7/1985 | Trokhan |
| 4,534,094 A | 8/1985 | Kessler |
| 4,550,681 A | 11/1985 | Zimmer et al. |
| 4,574,732 A | 3/1986 | Verwey et al. |
| 4,599,627 A | 7/1986 | Vollert |
| 4,637,859 A | 1/1987 | Trokhan |
| 4,738,674 A | 4/1988 | Todd et al. |
| 4,766,840 A | 8/1988 | Beckley et al. |
| 4,812,899 A | 3/1989 | Kueppers |
| 4,844,952 A | 7/1989 | Korenkiewicz et al. |
| 4,846,821 A | 7/1989 | Lyons et al. |
| 4,878,977 A | 11/1989 | Kueppers |
| 4,909,879 A | 3/1990 | Ball |
| 4,939,992 A | 7/1990 | Bird |
| 5,082,703 A | 1/1992 | Longobardi |
| 5,161,829 A | 11/1992 | Detrick et al. |
| 5,282,419 A | 2/1994 | Barrois |
| 5,288,348 A | 2/1994 | Modrak |
| 5,316,582 A | 5/1994 | Dubel |
| 5,332,613 A | 7/1994 | Taylor et al. |
| 5,354,289 A | 10/1994 | Mitchell et al. |
| 5,364,504 A | 11/1994 | Smurkoski et al. |
| 5,417,789 A | 5/1995 | Lauritzen |
| 5,429,686 A | 7/1995 | Chiu et al. |
| 5,458,590 A | 10/1995 | Schleinz et al. |
| 5,470,640 A | 11/1995 | Modrak |
| 5,503,076 A | 4/1996 | Yeo |
| 5,529,664 A | 6/1996 | Trokhan et al. |
| 5,549,790 A | 8/1996 | Van Phan |
| 5,556,509 A | 9/1996 | Trokhan et al. |
| 5,580,423 A | 12/1996 | Ampulski et al. |
| 5,609,725 A | 3/1997 | Van Phan |
| 5,629,052 A | 5/1997 | Trokhan et al. |
| 5,637,194 A | 6/1997 | Ampulski et al. |
| 5,672,248 A | 9/1997 | Wendt et al. |
| 5,674,663 A | 10/1997 | McFarland et al. |
| 5,679,222 A | 10/1997 | Rasch et al. |
| 5,693,187 A | 12/1997 | Ampulski et al. |
| 5,695,855 A | 12/1997 | Yeo et al. |
| 5,705,011 A | 1/1998 | Bodford et al. |
| 5,709,775 A | 1/1998 | Trokhan et al. |
| 5,714,041 A | 2/1998 | Ayers et al. |
| 5,733,634 A | 3/1998 | Karel |
| 5,734,800 A | 3/1998 | Herbert et al. |
| 5,766,389 A | 6/1998 | Brandon et al. |
| 5,776,307 A | 7/1998 | Ampulski et al. |
| 5,785,697 A | 7/1998 | Trombetta et al. |
| 5,795,440 A | 8/1998 | Ampulski et al. |
| 5,814,190 A | 9/1998 | Van Phan |
| 5,817,377 A | 10/1998 | Trokhan et al. |
| 5,846,379 A | 12/1998 | Ampulski et al. |
| 5,855,739 A | 1/1999 | Ampulski et al. |
| 5,858,514 A | 1/1999 | Bowers |
| 5,861,082 A | 1/1999 | Ampulski et al. |
| 5,865,950 A | 2/1999 | Vinson et al. |
| 5,871,887 A | 2/1999 | Trokhan et al. |
| 5,897,745 A | 4/1999 | Ampulski et al. |
| 5,900,109 A | 5/1999 | Sanders et al. |
| 5,904,811 A | 5/1999 | Ampulski et al. |
| 5,906,161 A | 5/1999 | Kessler |
| 5,906,710 A | 5/1999 | Trokhan |
| 5,942,085 A | 8/1999 | Neal et al. |
| 5,972,477 A | 10/1999 | Kim et al. |
| 5,990,377 A | 11/1999 | Chen |
| 6,033,513 A | 3/2000 | Nakamura |
| 6,048,938 A | 4/2000 | Neal et al. |
| 6,096,412 A | 8/2000 | McFarland et al. |
| 6,120,488 A | 9/2000 | Vanrijswijck et al. |
| 6,127,595 A | 10/2000 | Makoui et al. |
| 6,129,477 A | 10/2000 | Shoykhet |
| 6,173,646 B1 | 1/2001 | Tanaka et al. |
| 6,187,138 B1 | 2/2001 | Neal et al. |
| 6,234,078 B1 | 5/2001 | Kessler |
| 6,281,269 B1 | 8/2001 | Schut |
| 6,284,942 B1 | 9/2001 | Rabin |
| 6,307,119 B1 | 10/2001 | Cammarota et al. |
| 6,322,665 B1 | 11/2001 | Sun et al. |
| 6,330,857 B1 | 12/2001 | Maximovsky et al. |
| 6,350,711 B1 | 2/2002 | Potts |
| 6,403,857 B1 | 6/2002 | Gross et al. |
| 6,458,211 B1 | 10/2002 | Wefers et al. |
| 6,477,948 B1 | 11/2002 | Nissing et al. |
| 6,531,027 B1 | 3/2003 | Lender et al. |
| 6,572,575 B1 | 6/2003 | Shimada et al. |
| 6,610,131 B2 | 8/2003 | Harris et al. |
| 6,624,100 B1 | 9/2003 | Pike |
| 6,627,022 B2 | 9/2003 | Fusco |
| 6,651,560 B2 | 11/2003 | Neuhaus |
| 6,993,964 B2 | 2/2006 | Franz et al. |
| 7,306,699 B2 | 12/2007 | Urlaub et al. |
| 7,611,582 B2 | 11/2009 | McNeil et al. |
| 7,648,752 B2 | 1/2010 | Hoying et al. |
| 7,703,394 B2 | 4/2010 | Neuhaus |
| 7,736,688 B2 | 6/2010 | Oetjen et al. |
| 7,816,285 B2 | 10/2010 | MacDonald et al. |
| 8,012,297 B2 | 9/2011 | Baldauf |
| 8,153,226 B2 | 4/2012 | Curro et al. |
| 8,158,253 B2 | 4/2012 | Spinks |
| 8,163,132 B2 | 4/2012 | Kien |
| 8,691,041 B2 | 4/2014 | Oetjen |
| 8,943,957 B2 | 2/2015 | McNeil et al. |
| 8,945,334 B2 | 2/2015 | Oetjen |
| 9,050,220 B2 | 6/2015 | Digiacomantonio et al. |
| 9,102,182 B2 | 8/2015 | McNeil et al. |
| 9,237,973 B2 | 1/2016 | Abuto et al. |

(56) References Cited

U.S. PATENT DOCUMENTS

| | | |
|---|---|---|
| 9,414,971 B2 | 8/2016 | Oetjen |
| 9,579,924 B2 | 2/2017 | Boegli |
| 9,610,200 B2 | 4/2017 | Oetjen |
| 9,642,752 B2 | 5/2017 | Oetjen |
| 9,707,133 B2 | 7/2017 | Digiacomantonio et al. |
| 2001/0044611 A1 | 11/2001 | Noda et al. |
| 2002/0002358 A1 | 1/2002 | Durrance et al. |
| 2002/0058056 A1 | 5/2002 | Yahiaoui et al. |
| 2002/0087129 A1 | 7/2002 | Di et al. |
| 2002/0112832 A1 | 8/2002 | Burazin et al. |
| 2002/0138054 A1 | 9/2002 | Erdman |
| 2002/0143304 A1 | 10/2002 | Elder |
| 2002/0193765 A1 | 12/2002 | Kudo |
| 2003/0050618 A1 | 3/2003 | Kondo |
| 2003/0065299 A1 | 4/2003 | Carlucci et al. |
| 2003/0114818 A1 | 6/2003 | Benecke et al. |
| 2003/0124311 A1 | 7/2003 | Cree |
| 2003/0171729 A1 | 9/2003 | Kaun et al. |
| 2003/0194481 A1 | 10/2003 | Lippelt |
| 2004/0102750 A1 | 5/2004 | Jameson |
| 2004/0122386 A1 | 6/2004 | Mocadlo |
| 2004/0127872 A1 | 7/2004 | Petryk |
| 2004/0170813 A1 | 9/2004 | Digiacomantonio et al. |
| 2004/0176736 A1 | 9/2004 | Christon et al. |
| 2005/0177123 A1 | 8/2005 | Catalan |
| 2005/0281976 A1 | 12/2005 | Curro et al. |
| 2006/0008514 A1 | 1/2006 | Koenig et al. |
| 2006/0129115 A1* | 6/2006 | Visscher ............... A61F 15/001 604/361 |
| 2006/0135920 A1 | 6/2006 | Virgilio et al. |
| 2006/0201630 A1 | 9/2006 | Puffe et al. |
| 2007/0026209 A1 | 2/2007 | MacDonald et al. |
| 2007/0049153 A1 | 3/2007 | Dunbar et al. |
| 2007/0093770 A1 | 4/2007 | Ecker et al. |
| 2008/0036196 A1 | 2/2008 | Steenblik et al. |
| 2008/0132872 A1 | 6/2008 | Trennepohl et al. |
| 2010/0036352 A1 | 2/2010 | Hood et al. |
| 2010/0126366 A1 | 5/2010 | Kasper et al. |
| 2010/0206221 A1 | 8/2010 | Branca et al. |
| 2010/0209664 A1 | 8/2010 | Sato et al. |
| 2010/0222757 A1 | 9/2010 | Tee, Jr. |
| 2010/0233438 A1 | 9/2010 | Stone et al. |
| 2011/0106035 A1 | 5/2011 | Arora et al. |
| 2011/0112499 A1 | 5/2011 | Trennepohl et al. |
| 2011/0302733 A1 | 12/2011 | Yuan |
| 2012/0222568 A1 | 9/2012 | Byrne et al. |
| 2012/0296303 A1 | 11/2012 | Ng et al. |
| 2013/0197462 A1 | 8/2013 | Abuto et al. |
| 2014/0121621 A1 | 5/2014 | Kirby et al. |
| 2014/0180232 A1 | 6/2014 | Gagliardi et al. |
| 2014/0234575 A1 | 8/2014 | Mitsuno et al. |
| 2014/0296814 A1 | 10/2014 | Gray et al. |
| 2014/0324009 A1 | 10/2014 | Lee |
| 2015/0038933 A1 | 2/2015 | Day |
| 2015/0173964 A1 | 6/2015 | Coe et al. |
| 2015/0250662 A1 | 9/2015 | Isele et al. |
| 2015/0282997 A1 | 10/2015 | Arizti |
| 2015/0284892 A1 | 10/2015 | Galie et al. |
| 2015/0343480 A1 | 12/2015 | Byrne et al. |
| 2016/0067118 A1 | 3/2016 | Hammons et al. |
| 2016/0074251 A1 | 3/2016 | Strube et al. |
| 2016/0074252 A1 | 3/2016 | Strube et al. |
| 2016/0074253 A1 | 3/2016 | Strube et al. |
| 2016/0074254 A1 | 3/2016 | Orr et al. |
| 2016/0074255 A1 | 3/2016 | Strube et al. |
| 2016/0074256 A1 | 3/2016 | Strube et al. |
| 2016/0075122 A1 | 3/2016 | Strube et al. |
| 2016/0075123 A1 | 3/2016 | Strube et al. |
| 2016/0076180 A1 | 3/2016 | Strube et al. |
| 2016/0076181 A1 | 3/2016 | Strube et al. |
| 2016/0076182 A1 | 3/2016 | Strube et al. |
| 2016/0076184 A1 | 3/2016 | Orr et al. |
| 2016/0129661 A1 | 5/2016 | Arora |
| 2016/0331596 A1 | 11/2016 | Oetjen |
| 2017/0119591 A1 | 5/2017 | Noel |
| 2017/0120260 A1 | 5/2017 | Oetjen |
| 2017/0210110 A1 | 7/2017 | Oetjen |
| 2017/0225449 A1* | 8/2017 | Aviles .................... B41F 21/00 |
| 2017/0258650 A1 | 9/2017 | Rosati et al. |
| 2017/0258651 A1 | 9/2017 | Hammons |
| 2017/0259524 A1 | 9/2017 | Neton et al. |
| 2017/0259550 A1 | 9/2017 | Neton et al. |
| 2018/0071151 A1* | 3/2018 | Aviles ............... A61F 13/51104 |
| 2019/0110939 A1 | 4/2019 | Hammons et al. |
| 2020/0038263 A1 | 2/2020 | Aviles et al. |

FOREIGN PATENT DOCUMENTS

| | | | |
|---|---|---|---|
| CN | 104975365 A | 10/2015 | |
| DE | 19854634 C1 | 2/2000 | |
| EP | 0165807 A1 | 12/1985 | |
| EP | 0951889 A1 | 10/1999 | |
| EP | 1338262 A1 | 8/2003 | |
| EP | 1527898 A1 | 5/2005 | |
| EP | 1075948 B1 | 11/2005 | |
| EP | 0959842 B2 | 6/2006 | |
| EP | 1673225 B1 | 8/2008 | |
| EP | 2745823 A1 | 6/2014 | |
| GB | 1176321 | 1/1970 | |
| GB | 1241793 | 8/1971 | |
| GB | 1241794 | 8/1971 | |
| GB | 1350059 | 4/1974 | |
| GB | 1396282 | 6/1975 | |
| GB | 1439458 | 6/1976 | |
| GB | 1468360 | 3/1977 | |
| GB | 1570545 | 7/1980 | |
| GB | 2314292 A1 | 12/1997 | |
| WO | WO8400516 A1 | 2/1984 | |
| WO | WO9954143 A1 | 10/1999 | |
| WO | WO-0064502 A1 * | 11/2000 | ............ A61L 15/34 |
| WO | WO03020835 A1 | 3/2003 | |
| WO | WO2007070132 A1 | 6/2007 | |
| WO | WO2008103650 A2 | 8/2008 | |
| WO | 2009062998 A1 | 5/2009 | |
| WO | WO2010071543 A1 | 6/2010 | |
| WO | WO2012176656 A1 | 12/2012 | |

OTHER PUBLICATIONS

Search Report and Written Opinion for PCT/US2017/016324 dated May 30, 2017.
International Search Report for PCT/US2017/021485 dated May 18, 2017.
Search Report and Written Opinion for PCT/US2017/050603 dated Nov. 7, 2017.
PCT Search Report and Written Opinion dated Oct. 2, 2019.
Hatch, Kathryn, "Nonwoven Fabrics Structures", Textile Science, 1993, p. 363.
All Office Actions for U.S. Appl. No. 15/698,709 filed Sep. 8, 2017.
All Office Actions for U.S. Appl. No. 15/453,981 filed Mar. 9, 2017.
All Office Actions, U.S. Appl. No. 16/529,816.

* cited by examiner

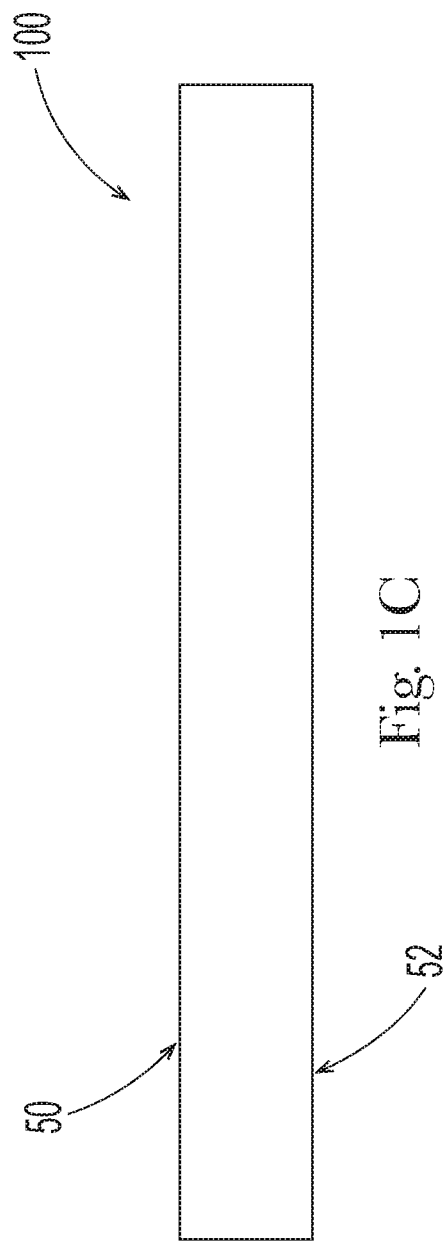

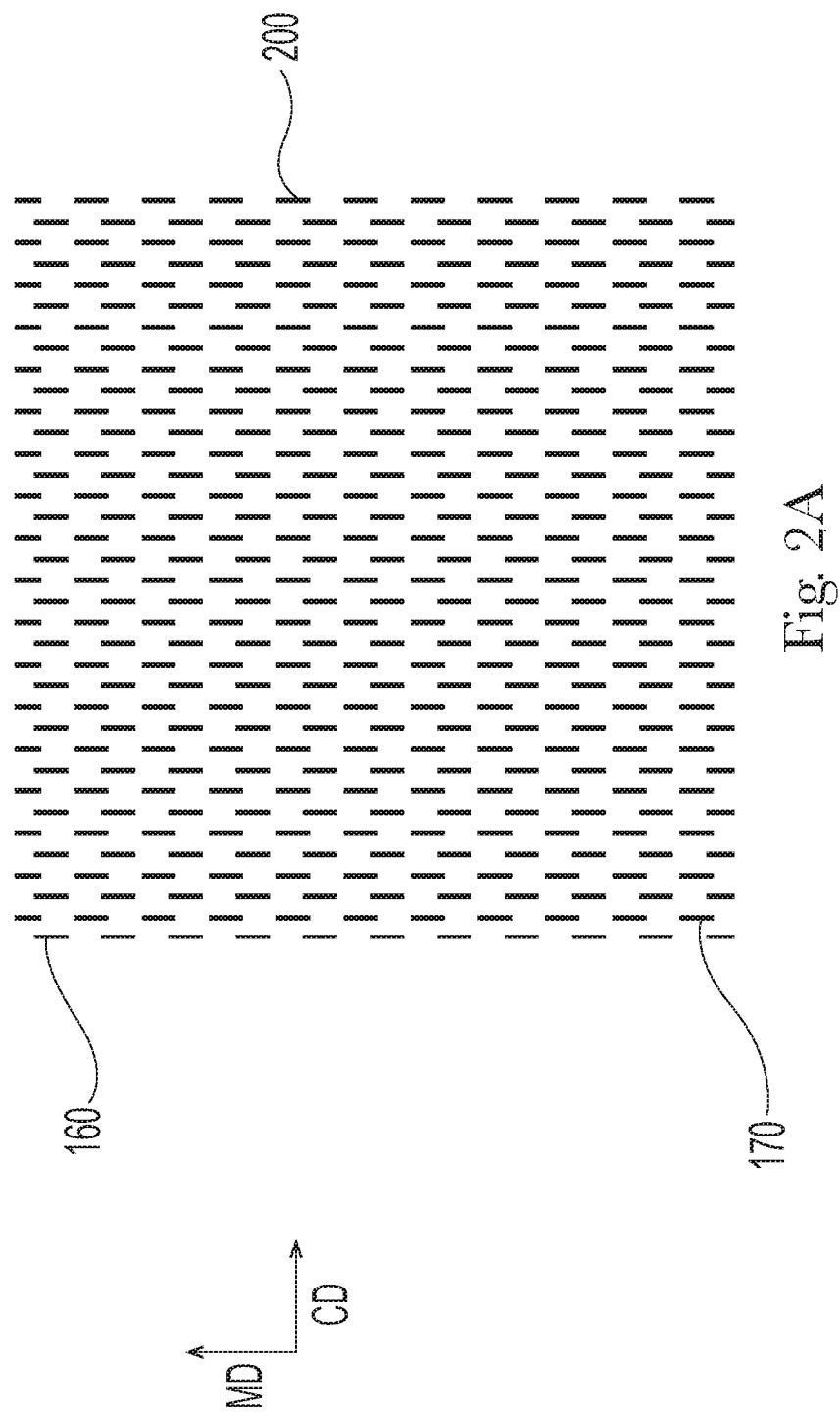

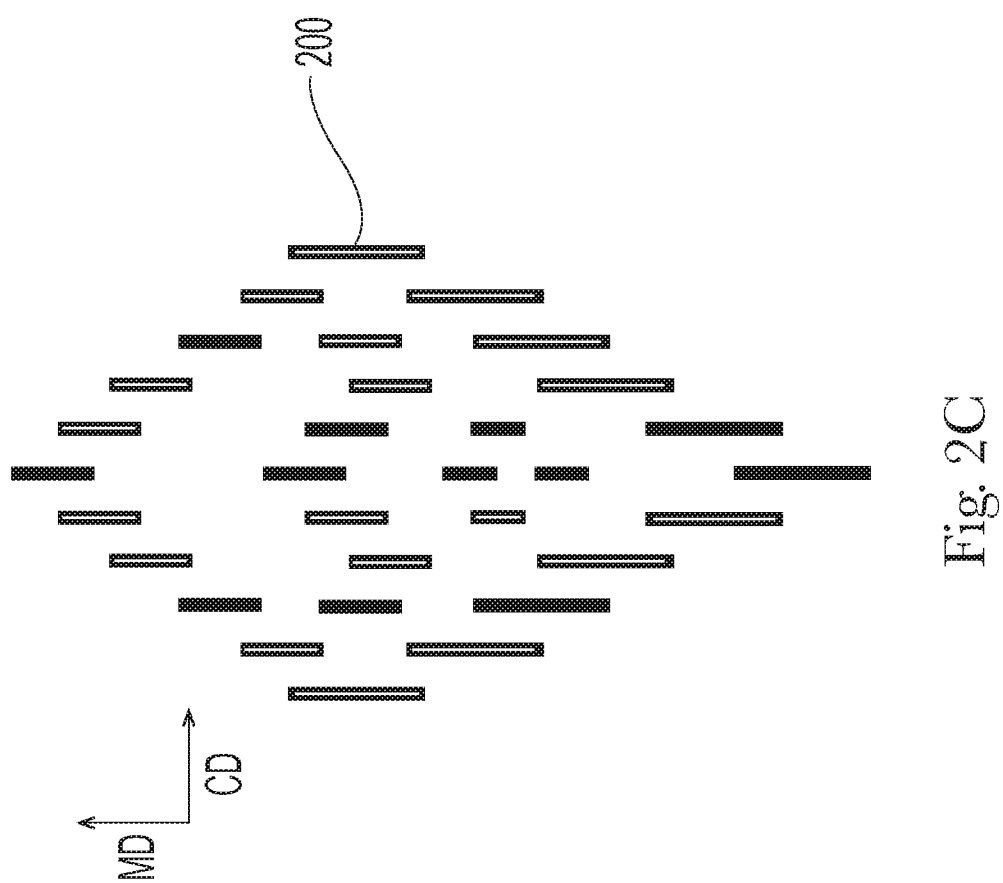

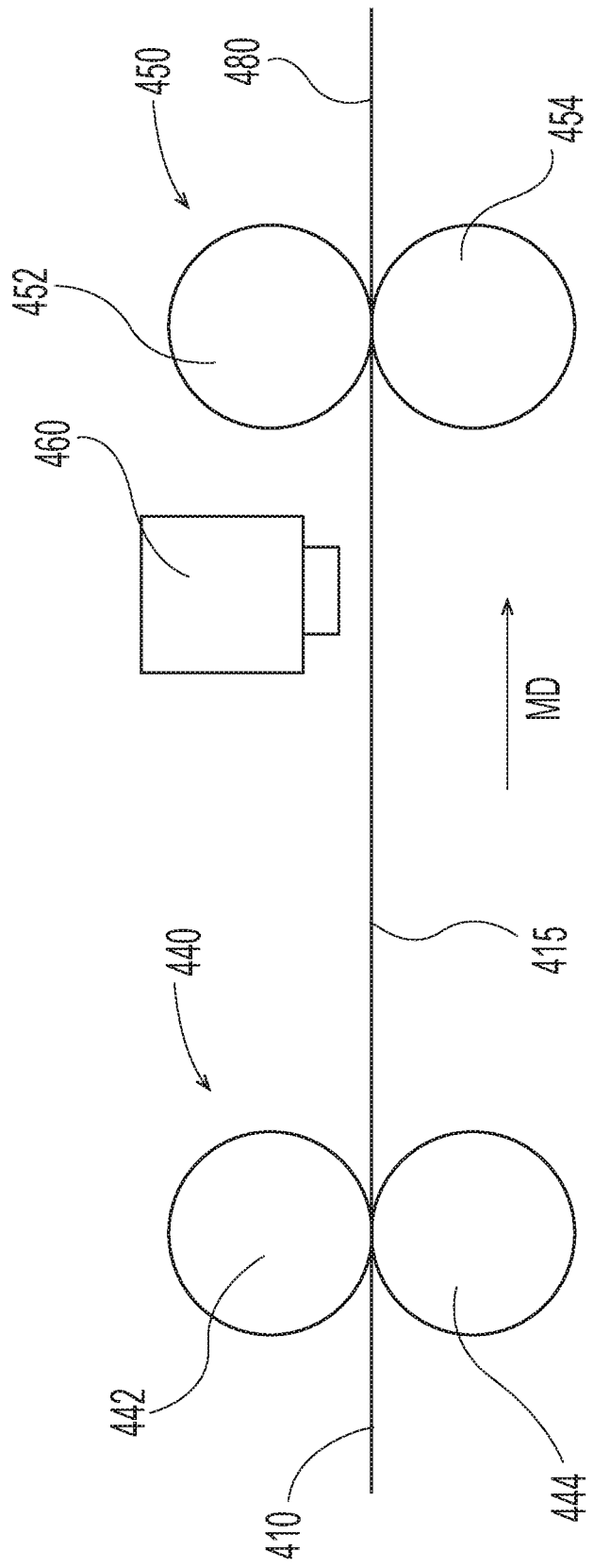

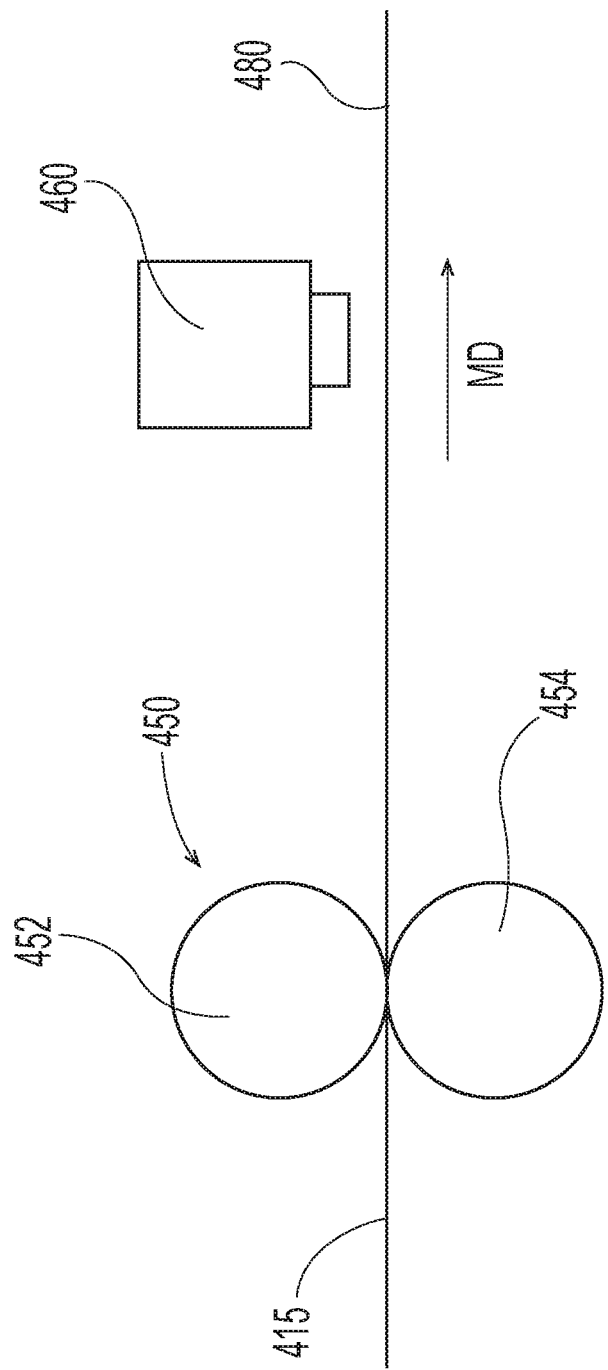

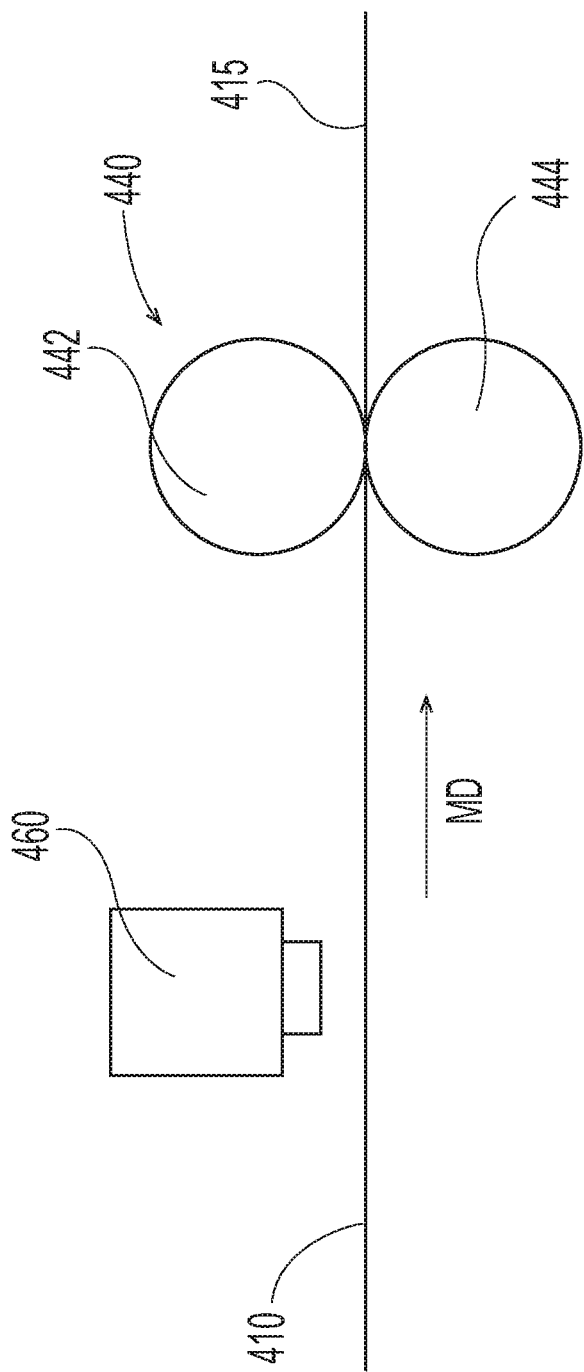

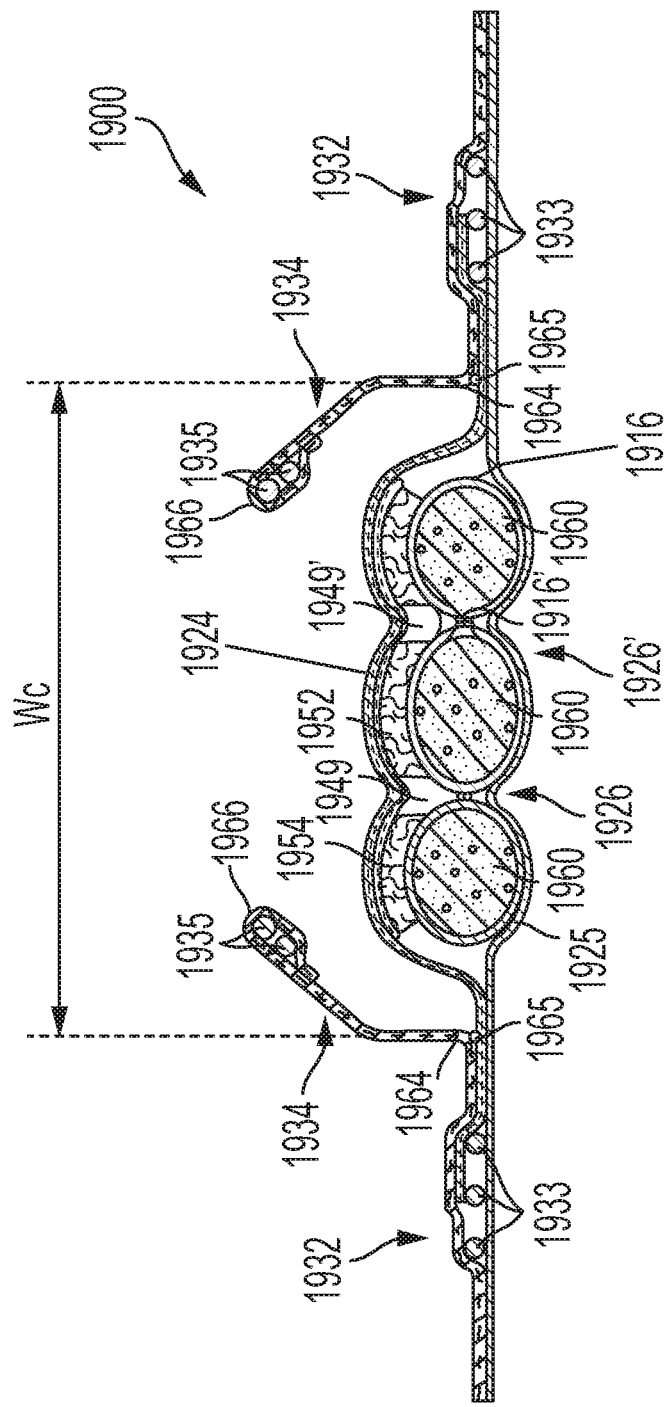

WEBS WITH COMPOSITIONS APPLIED THERETO

FIELD OF THE INVENTION

The present invention pertains to webs having a plurality of composition elements applied thereto.

BACKGROUND OF THE INVENTION

Nonwovens, films, and laminates thereof are widely used in disposable absorbent article manufacturing. For example, some commercially available disposable absorbent articles utilize a nonwoven topsheet and others utilize a film topsheet. Some disposable absorbent articles utilize a nonwoven/film laminate backsheet.

In general, there are three primary functions of a topsheet of a disposable absorbent article which can be condensed into three specific performance attributes. First, the topsheet desirably acquires liquid insults in a reasonable time. This can cut down on the wet feeling that a user perceives when liquid is impinged upon the topsheet. Second, acquired liquid insults, once drained from the topsheet, should desirably be discouraged from rewetting the topsheet when pressure is applied to the absorbent article. Third, particularly in the case of feminine sanitary pads, the topsheet desirably disguises menstrual fluid in the pad to some extent making the menstrual fluid less noticeable to the wearer.

Unfortunately, acquisition and rewet can present diametrically opposed interests. For example, efforts to minimize acquisition speed often can result in a higher rewet. Similarly, efforts to minimize rewet are often at the cost of increased acquisition speeds. And unfortunately, a similar inverse relationship can exist between acquisition and masking.

Based on the foregoing, there is a need for material that can achieve both good acquisition speed, good rewet performance, and good masking performance. Similarly, there is a need for a method of making such materials. And, there is a need for a method which is flexible enough to address varying desires depending on the products to which the materials are being applied.

SUMMARY OF THE INVENTION

The present invention provides webs having a composition or a plurality of compositions thereon. The present invention also provides systems and methods for providing compositions to the web. In one particular example, an absorbent article comprises a longitudinal centerline and a lateral centerline, a machine direction (MD) generally oriented parallel to the longitudinal centerline and a cross direction (CD) generally oriented parallel to the lateral centerline. The absorbent article further comprises: a topsheet having a first surface and a second surface, the topsheet comprising a nonwoven material made up of a plurality of filaments or fibers; a backsheet; an absorbent core disposed between the topsheet and the backsheet; a plurality of composition elements disposed on the topsheet, wherein each of the composition elements comprise an element width and an element spacing between adjacent elements, wherein a ratio of element spacing to element width is between about 0.5 to about 8, between about 0.7 to about 2.1, between about 1.1 to about 1.9, or between about 1.4 to about 1.7 as measured by the Composition Pattern Analysis method.

In another example, an array of products may be provided. The array of absorbent articles comprises a first absorbent article and a second absorbent article, each of the first absorbent article and the second absorbent article comprising a topsheet, a backsheet, an absorbent core disposed between the topsheet and the backsheet, and a first plurality of composition elements applied to a first topsheet of the first absorbent article and a second plurality of composition elements applied to a second topsheet of the second absorbent article, wherein the first plurality of composition elements has a first ratio of composition element spacing to composition element width as measured by the Composition Pattern Analysis, and the second plurality of composition elements has a second ratio of composition element spacing to composition element width as measured by the Composition Pattern Analysis, and wherein the first ratio is different than the second ratio.

BRIEF DESCRIPTION OF THE DRAWINGS

FIG. 1C is an exaggerated side view of the web of FIG. 1A or 1B showing the surfaces thereof.

FIGS. 2A-2C are schematic illustrations showing bond patterns for creating melt stabilized areas in the webs of the present disclosure.

FIGS. 4A-4C are schematic illustrations showing exemplary processes for making webs in accordance with the present disclosure.

FIG. 8 is a schematic illustration showing the cross-sectional view of FIG. 7 in expanded form.

DETAILED DESCRIPTION OF THE INVENTION

Figure 1A:
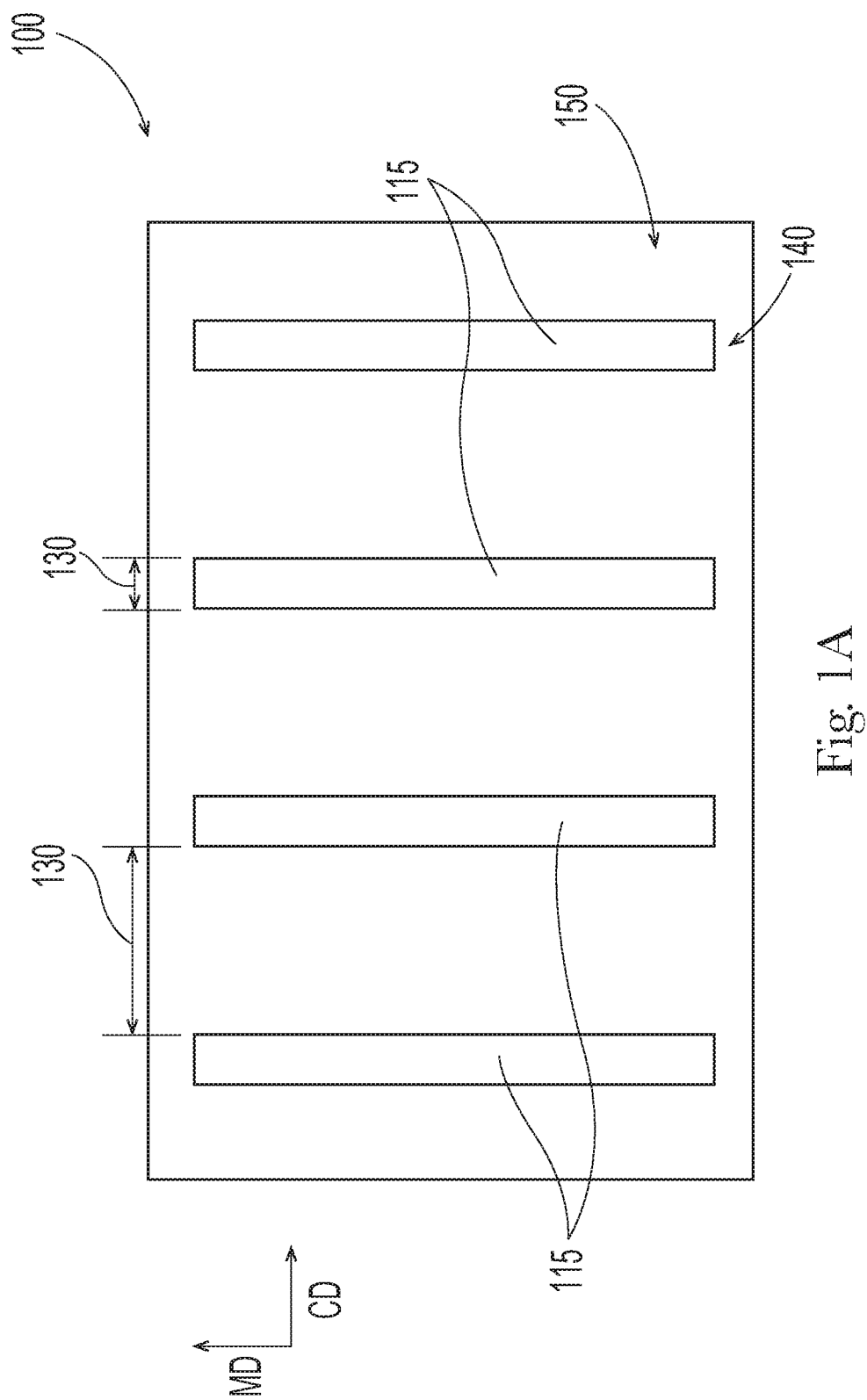
FIGS. 1A and 1B are schematic representations of a web constructed in accordance with the present disclosure.

As used herein "hydrophilic" and "hydrophobic" have meanings as well established in the art with respect to the contact angle of water on the surface of a material. Thus, a material having a water contact angle of greater than about 90 degrees is considered hydrophobic, and a material having a water contact angle of less than about 90 degrees is considered hydrophilic. Compositions which are hydrophobic, will increase the contact angle of water on the surface of a material while compositions which are hydrophilic will decrease the contact angle of water on the surface of a material. Notwithstanding the foregoing, reference to relative hydrophobicity or hydrophilicity between a material and a composition, between two materials, and/or between two compositions, does not imply that the materials or compositions are hydrophobic or hydrophilic. For example, a composition may be more hydrophobic than a material. In such a case neither the composition nor the material may be hydrophobic; however, the contact angle exhibited by the composition is greater than that of the material. As another example, a composition may be more hydrophilic than a material. In such a case, neither the composition nor the material may be hydrophilic; however, the contact angle exhibited by the composition may be less than that exhibited by the material The contact angle of a material web and/or composition on a material web can be determined via the Contact Angle method disclosed herein.

"Array" means a display of packages comprising disposable articles of different sizes having like article constructions (e.g., same elastomeric materials [compositionally and/or structurally] in the flaps, graphic elements) said packages having the same brand and/or sub-brand, and said packages oriented in proximity to each other in a given area of a retail store. An array is marketed as a line-up of products normally having like packaging elements (e.g., packaging material type, film, paper, dominant color, design theme, etc.) that convey to consumers that the different individual packages are part of a larger line-up. Arrays often have the same brand, for example, "Depend," and same sub-brand, for example, "for Women Underwear." A different array may have the brand "Depend" and the sub-brand "Silhouette For Women." The differences between the "for Women Underwear" array and the "Silhouette For Women" arrays include different elastomeric materials in the side flaps, where "for Women Underwear" comprises strands as the elastomeric material and "Silhouette For Women" comprises a film elastomeric material." Furthermore, the packaging is distinctly different in that "for Women Underwear" is packaged in a predominately green, film bag and "Silhouette For Women" is packaged in a predominately maroon box.

Further regarding "Arrays," as another example of two separate "arrays" having the same brand, "Certainty," one line-up has the sub-brand "Women's Underwear." A different array may have the same brand "Certainty" and the sub-brand "Smooth Shape Briefs for Women." The differences between the "Women's Underwear" array and the "Smooth Shape Briefs for Women" arrays include different elastomeric materials in the side flaps, where "Women's Underwear" comprises strands as the elastomeric material and "Smooth Shape Briefs for Women" comprises a film elastomeric material." Furthermore, the packaging is distinctly different in that "Women's Underwear" is packaged in a predominately blue, film bag and "Smooth Shape Briefs for Women" is packaged in a predominately maroon box.

Arrays also often have the same trademarks, including trademarks of the brand, sub-brand, and/or features and/or benefits across the line-up.

"On-line Array" means an "Array" distributed by a common on-line source.

The webs of the present disclosure can provide a balance between acquisition speed, rewet, and masking. The webs of the present disclosure may comprise a plurality of fibers comprised of a thermoplastic polymeric material. The webs of the present invention further comprise a plurality of composition elements, wherein the composition elements are more hydrophilic or more hydrophobic than the thermoplastic polymeric material of the web. The plurality of composition elements may be printed in a manner which balances acquisition, rewet, and masking. The arrangement of composition elements is described in additional detail below.

Figure 1B:
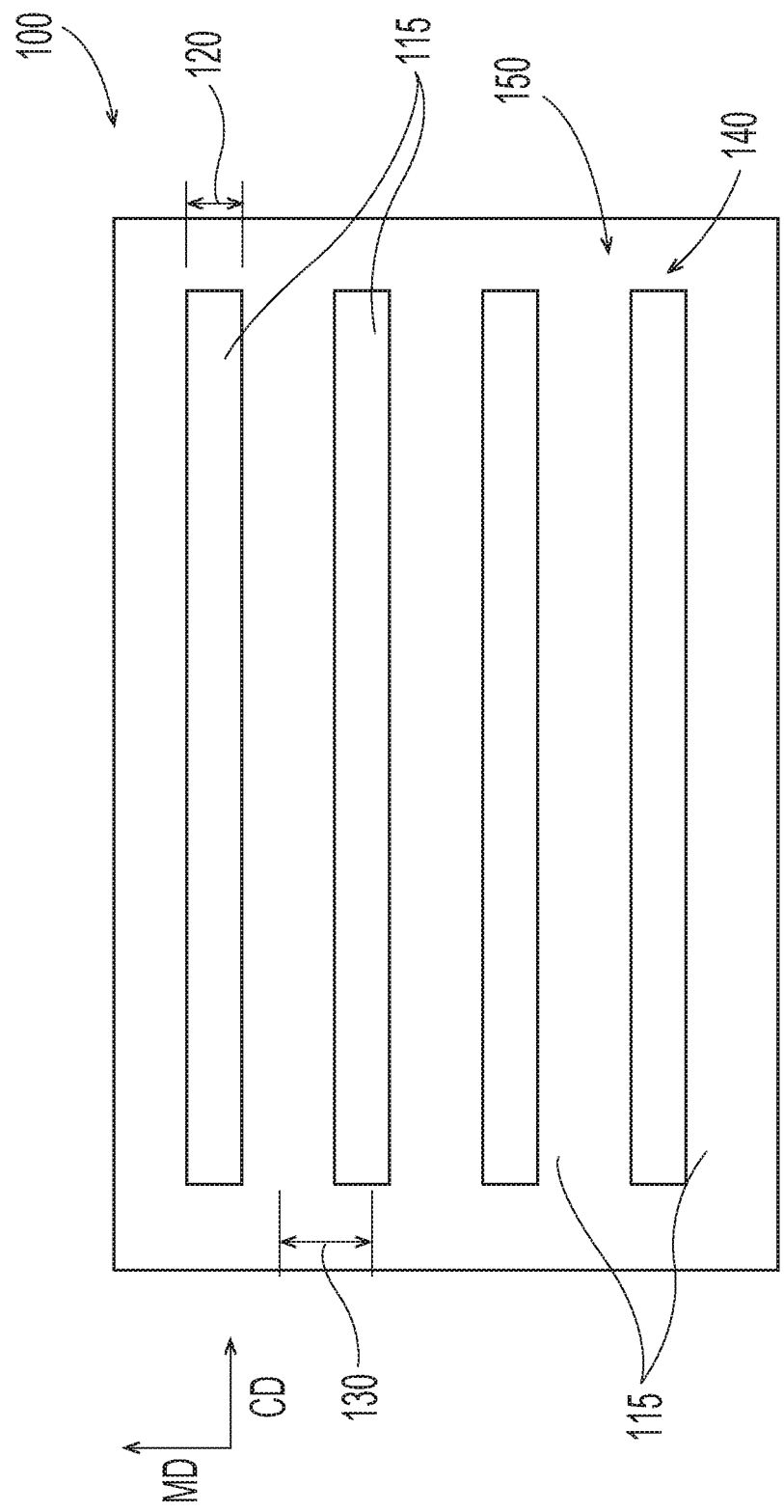

As shown in FIGS. 1A and 1B, a web 100, in accordance with the present disclosure, comprises a machine direction "MD", and a cross machine direction "CD." The terms "MD" and "CD" are well known in the art. A plurality of composition elements 115, e.g. stripes, are deposited on the web 100. Each of the composition elements 115 comprises a composition element width 120 and a composition element spacing 130. The composition element spacing 130 is determined as disclosed in the test method entitled "Composition Pattern Analysis" under the subsection "Pattern Spacing Measurements." As shown in FIG. 1A, the composition element width 120 may be generally parallel to the CD, and the composition element spacing 130 may similarly be generally parallel to the CD. In contrast, the composition elements 115 may be arranged in the CD, as shown in FIG. 1B, and as such, the composition element width 120 may be generally parallel to the MD, and the composition element spacing 130 may similarly be generally parallel to the MD.

As noted previously, the composition elements 115 comprise a composition which is more hydrophilic or more hydrophobic than the thermoplastic polymeric material of the web 100. With the provision of the composition elements 115, the web 100 comprises treated areas 140 and untreated areas 150. The untreated areas 150 of the web 100 correspond to those areas which do not comprise a composition element 115, e.g. between adjacent composition elements 115. In contrast, the treated areas 140 of the web 100 correspond to those areas which comprise a composition element 115.

The inventors have surprisingly found that the composition element width 120 and the composition element spacing 130 can impact fluid performance properties of the web 100. For example, the time to acquire fluid insults can be impacted by the above factors. The amount of liquid rewet is also impacted by the above factors. And last, the stain saturation of the fluid insult in an absorbent article can similarly be impacted by the above factors. Samples were created and tested regarding these three factors and are described below in detail. Acquisition and rewet can be determined via the Acquisition Time and Rewet Method disclosed herein. Stain saturation can be determined via the Stain perception measurement method disclosed herein.

As shown in FIG. 1C, the webs 100 comprise a first surface 50 and an opposing second surface 52. The webs 100 may comprise apertures 110 which extend from the first surface 50 through the second surface 52. And much like discussed previously, the composition elements 115 may extend in the MD or CD.

Figure 1D:
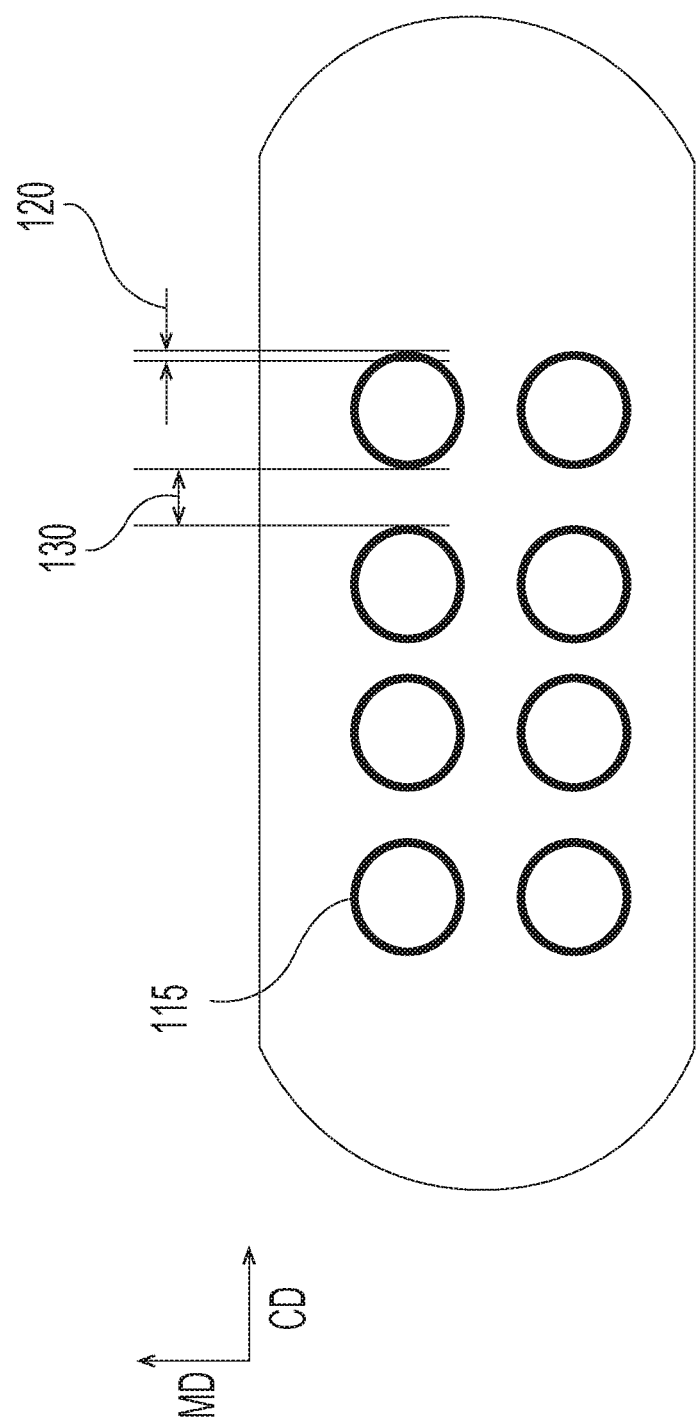
FIGS. 1D and 1E are schematic representations of articles having exemplary composition elements thereon.
Figure 1E:
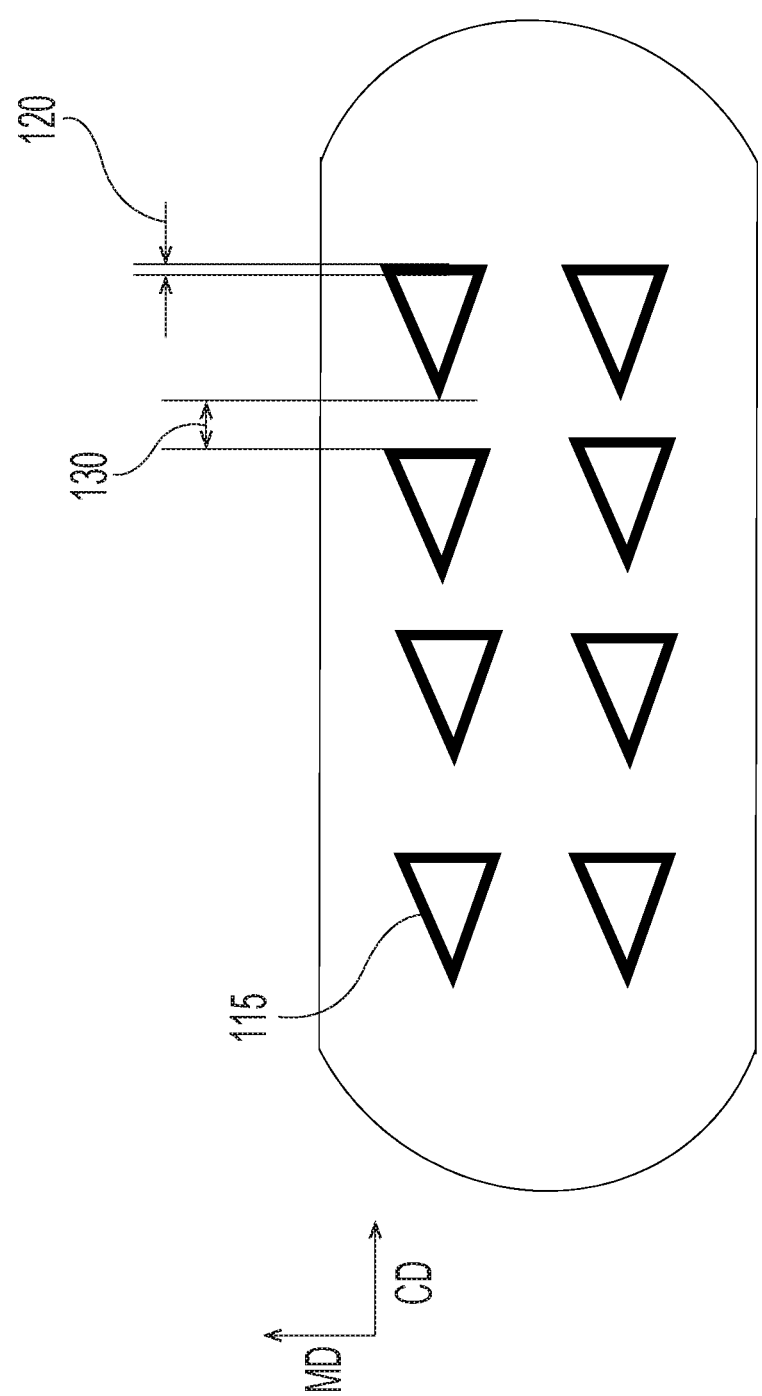

While the composition elements 115 were shown as stripes in FIGS. 1A and 1B, the composition elements 115 may comprise any suitable shape. For example, FIGS. 1D and 1E show composition elements 115 that may comprise circles and triangles. However, these are simply additional examples. It is believed that the thickness 120 of the composition elements 115 as well as the minimum spacing 130 between adjacent composition elements 115 are critical in effecting the acquisition speed, rewet potential, and stain masking. The determination of the shape of the composition elements as well as the spacing, location, etc. can be determined via the Composition Pattern Analysis method disclosed herein.

Samples

Many samples were prepared and tested regarding acquisition, rewet, and staining. Each of the samples comprised a topsheet. Each topsheet was a 25 gsm nonwoven web comprising spunbond bi-component filaments with a hydrophobic melt additive. The melt additive was glycerol tristearate at about 2 percent loading of the overall fiber. The bi-component filaments were polyethylene/polypropylene, core/sheath configuration with the polyethylene in the sheath. The filaments were 30 percent by weight polyethylene and 70 percent by weight polypropylene with the glycerol tristearate in the sheath.

Nonwoven webs which were apertured comprised one of three aperture patterns. Aperture pattern 1 was performed in accordance with processes disclosed in U.S. Pat. Nos. 5,658, 639; 5,628,097; 5,916,661; 7,917,985; and U.S. Patent Application Publication No. 2003/0021951. Namely, the nonwoven webs were subjected to a bonding process where the web is compressed under high pressure to create a plurality of melt stabilized areas in the nonwoven web. Bond patterns which create the melt stabilized areas 200 for aperture pattern 1 are shown in FIG. 2A. The bond pattern as shown, was formed via a plurality of nubs which correspond to the melt stabilized areas. Each of the melt stabilized areas were 2.54 mm long in the MD by 0.25 mm wide in the CD and spaced apart (center-to-center) by about 1.525 mm to the next melt stabilized area. The melt stabilized area density was about 12.9 melt stabilized areas per square cm. The nubs and therefore the resulting melt stabilized areas 200 were staggered in columns such that apertures in a first column 160 were positioned immediately adjacent to apertures in a second column 170. However, the apertures of the second column were staggered from the apertures in the first column 160 such that apertures in the first columns 160 formed rows oriented in the CD and apertures in the second columns 170 formed adjacent rows oriented in the CD. Subsequent to the bonding process, the webs were then stretched in the CD to break the majority, if not all, of the melt stabilized areas thereby forming apertures.

Figure 2B:
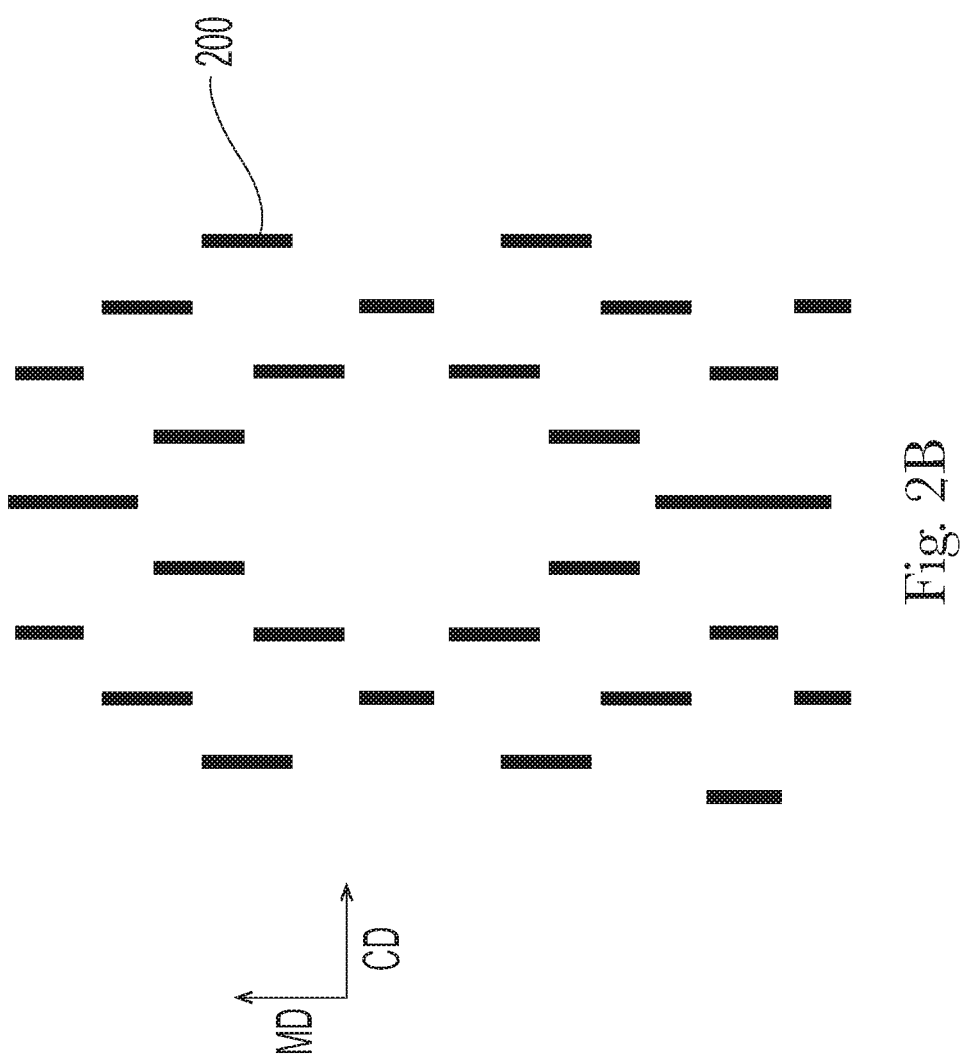

For those nonwoven webs which comprised aperture patterns 2 and 3, these webs were apertured in accordance with US Patent Application Publication Nos. 2016/0129661, 2016/0167334, and 2016/0278986. Much like the process above, these nonwoven webs were subjected to a bonding process where the web was compressed under high pressure to create a plurality of melt stabilized areas in the nonwoven web. Bond patterns utilized to create melt stabilized areas are shown in FIGS. 2B and 2C which correspond to aperture patterns 2 and 3, respectively. As shown, a plurality of nubs corresponding to the melt stabilized areas 200 can be utilized. In such aperture patterns the columns and rows of apertures may be variable from column to column and row to row.

Each of these nonwoven webs served as a topsheet for a corresponding Sample. Each of the nonwoven webs was combined with a secondary topsheet and an absorbent core to form a plurality of absorbent articles. The secondary topsheet was a 75 gsm spunlace nonwoven web. The absorbent core was an airlaid core having a basis weight of 200 gsm. Each of the secondary topsheet and absorbent core are available in current Always™ Ultra Thin pads.

Each of the plurality of sample absorbent articles above was cut into rectangular shape 63.5 mm by 76.2 mm creating a plurality of absorbent article samples. Fluid insults were introduced to each of the samples. Acquisition and rewet were measured. For stain intensity, images were taken after three 1 ml insults.

Samples 1-8 associated with Tables 1 and 2, comprised Aperture pattern 1 and had compositional elements, i.e. stripes, which were applied via a Galaxy Phase Change online Printer. The composition was applied to the nonwoven web subsequent to the formation of the melt stabilized areas in the nonwoven web. Subsequently, the nonwoven web was stretched in the CD which broke the melt stabilized areas thereby forming the apertures in the nonwoven web. And, the stretching in the CD also modified the element width for those elements which were oriented in the MD. Additional data is provided in this regard in Table 9. Acquisition, rewet, and masking data regarding samples 1-8 is provided in Table 2. Sample 8 is a control for the testing of the samples. Sample 8 comprised no composition applied thereto.

TABLE 1

| Sample No. | Composition Stripe Orientation | Composition Stripe Width (mm) | Composition Stripe Spacing (mm) | Ratio Spacing/Width |
|---|---|---|---|---|
| 1 | MD | 0.5 | 1 | 2 |
| 2 | MD | 0.5 | 2 | 4 |
| 3 | MD | 1 | 1 | 1 |
| 4 | MD | 1 | 2 | 2 |
| 5 | MD | 1 | 4 | 4 |
| 6 | MD | 2 | 2 | 1 |
| 7 | MD | 2 | 4 | 2 |
| 8 | Control B | na | na | na |

TABLE 2

| Sample No. | Avg Acq 1 (s) | Avg Acq 2 (s) | Avg Acq 3 (s) | Avg Rewet (g) | Chroma | Interface Fluid Area (mm^2) |
|---|---|---|---|---|---|---|
| 1 | 8.7 | 9.3 | 9.3 | 0.496 | 14.5 | 248.9 |
| 2 | 11.0 | 12.0 | 13.7 | 0.472 | 11.3 | 144.9 |
| 3 | 5.7 | 6.3 | 7.3 | 0.594 | 18.0 | 484.4 |
| 4 | 7.0 | 8.3 | 9.7 | 0.587 | 14.0 | 311.9 |
| 5 | 10.0 | 12.7 | 15.3 | 0.515 | 11.4 | 170.6 |
| 6 | 5.3 | 6.7 | 8.0 | 0.645 | 16.7 | 436.2 |
| 7 | 7.7 | 7.7 | 8.7 | 0.549 | 14.2 | 291.9 |
| 8 | 22.7 | 32.7 | 35.0 | 0.428 | 10.3 | 136.5 |

Samples 9-16 comprised Aperture pattern 2 and were provided with compositional elements, i.e. stripes, as noted in Tables 3 and 4 below, utilizing a Galaxy Phase Change online Printer. The composition was applied to the nonwoven web subsequent to the formation of the melt stabilized areas in the nonwoven web. Subsequently, the nonwoven web was stretched in the CD which broke the melt stabilized areas thereby forming the apertures in the nonwoven web. And, similar to the above Samples, the stretching in the CD also modified the element width for those stripes which were oriented in the MD. Additional data is provided in this regard in Table 9. Acquisition, rewet, and masking data regarding samples 9-16 is provided in Table 4. Sample 16 is a control for the testing of the samples. Sample 16 comprised no composition applied thereto.

TABLE 3

| Sample No. | Composition Stripe Orientation | Composition Stripe Width (mm) | Composition Stripe Spacing (mm) | Ratio Spacing/Width |
|---|---|---|---|---|
| 9 | MD | 0.5 | 1 | 2 |
| 10 | MD | 0.5 | 2 | 4 |
| 11 | MD | 1 | 1 | 1 |
| 12 | MD | 1 | 2 | 2 |
| 13 | MD | 1 | 4 | 4 |
| 14 | MD | 2 | 2 | 1 |
| 15 | MD | 2 | 4 | 2 |
| 16 | Control C | na | na | na |

TABLE 4

| Sample No. | Avg Acq 1 (s) | Avg Acq 2 (s) | Avg Acq 3 (s) | Avg Rewet (g) | Chroma | Interface Fluid Area (mm^2) |
|---|---|---|---|---|---|---|
| 9  | 24.7 | 17.0 | 23.3 | 0.431 | 8.6  | 111.4 |
| 10 | 40.3 | 32.7 | 34.3 | 0.388 | 8.1  | 97.3  |
| 11 | 11.0 | 12.7 | 13.7 | 0.508 | 11.7 | 181.9 |
| 12 | 16.0 | 16.7 | 18.3 | 0.529 | 9.2  | 103.9 |
| 13 | 13.7 | 16.7 | 18.3 | 0.523 | 9.2  | 138.9 |
| 14 | 8.0  | 9.0  | 10.3 | 0.681 | 12.1 | 259.9 |
| 15 | 10.0 | 11.7 | 13.0 | 0.600 | 10.6 | 203.6 |
| 16 | 67.3 | 77.7 | 87.0 | 0.388 | 8.6  | 154.8 |

Samples 17-24 comprised Aperture pattern 3 and were provided with compositional elements, i.e. stripes, as noted in Tables 5 and 6 below, utilizing a Galaxy Phase Change online Printer. The composition was applied to the nonwoven web subsequent to the formation of the melt stabilized areas in the nonwoven web. Subsequently, the nonwoven web was stretched in the CD which broke the melt stabilized areas thereby forming the apertures in the nonwoven web. And, similar to the above Samples, the stretching in the CD also modified the element width for those stripes which were oriented in the MD. Additional data is provided in this regard in Table 9. Acquisition, rewet, and masking data regarding samples 17-24 is provided in Table 6. Sample 24 is a control for the testing of the samples. Sample 24 comprised no composition applied thereto.

TABLE 5

| Sample No. | Composition Stripe Orientation | Composition Stripe Width (mm) | Composition Stripe Spacing (mm) | Ratio Spacing/Width |
|---|---|---|---|---|
| 17 | MD | 0.5 | 1  | 2  |
| 18 | MD | 0.5 | 2  | 4  |
| 19 | MD | 1   | 1  | 1  |
| 20 | MD | 1   | 2  | 2  |
| 21 | MD | 1   | 4  | 4  |
| 22 | MD | 2   | 2  | 1  |
| 23 | MD | 2   | 4  | 2  |
| 24 | Control D | na | na | na |

TABLE 6

| Sample No. | Avg Acq 1 (s) | Avg Acq 2 (s) | Avg Acq 3 (s) | Avg Rewet (g) | Chroma | Interface Fluid Area (mm^2) |
|---|---|---|---|---|---|---|
| 17 | 8.0  | 9.3  | 9.7  | 0.622 | 17.0 | 405.6 |
| 18 | 11.0 | 14.3 | 16.3 | 0.494 | 12.4 | 197.9 |
| 19 | 5.7  | 6.7  | 8.0  | 0.653 | 21.0 | 601.7 |
| 20 | 7.3  | 9.7  | 11.3 | 0.595 | 15.7 | 367.0 |
| 21 | 10.7 | 12.0 | 13.3 | 0.632 | 13.5 | 278.7 |
| 22 | 6.3  | 7.7  | 8.3  | 0.709 | 17.8 | 490.0 |
| 23 | 6.3  | 8.3  | 10.0 | 0.632 | 15.1 | 344.1 |
| 24 | 15.3 | 21.7 | 27.3 | 0.480 | 10.8 | 210.8 |

Samples 25-37 comprised no apertures and were provided with compositional elements, i.e. stripes, as noted in Tables 7 and 8 below, utilizing a Galaxy Phase Change online Printer. Acquisition, rewet, and masking data regarding samples 25-37 is provided in Table 8.

TABLE 7

| Sample No. | Composition Stripe Orientation | Composition Stripe Width (mm) | Composition Stripe Spacing (mm) | Ratio Spacing/Width |
|---|---|---|---|---|
| 25 | MD | 0.5 | 0.5 | 1   |
| 26 | MD | 0.5 | 1   | 2   |
| 27 | MD | 0.5 | 2   | 4   |
| 28 | MD | 0.5 | 4   | 8   |
| 29 | MD | 1   | 1   | 1   |
| 30 | MD | 1   | 2   | 2   |
| 31 | MD | 1   | 4   | 4   |
| 32 | MD | 2   | 2   | 1   |
| 33 | MD | 2   | 4   | 2   |
| 34 | MD | 2   | 8   | 4   |
| 35 | MD | 4   | 2   | 0.5 |
| 36 | MD | 4   | 4   | 1   |
| 37 | MD | 4   | 8   | 2   |

TABLE 8

| Sample No. | Avg Acq 1 (s) | Avg Acq 2 (s) | Avg Acq 3 (s) | Avg Rewet (g) | Chroma | Interface Fluid Area (mm^2) |
|---|---|---|---|---|---|---|
| 25 | 8  | 8  | 11 | 0.66 | 18.2 | 474.6 |
| 26 | 11 | 11 | 14 | 0.55 | 13.0 | 239.0 |
| 27 | 16 | 18 | 27 | 0.55 | 8.8  | 120.1 |
| 28 | 17 | 24 | 42 | 0.46 | 10.4 | 176.9 |
| 29 | 7  | 10 | 12 | 0.73 | 16.5 | 408.5 |
| 30 | 11 | 12 | 15 | 0.59 | 12.4 | 234.2 |
| 31 | 12 | 18 | 29 | 0.57 | 10.5 | 179.3 |
| 32 | 6  | 9  | 11 | 0.74 | 18.4 | 490.0 |
| 33 | 8  | 12 | 16 | 0.64 | 12.9 | 263.1 |
| 34 | 8  | 12 | 15 | 0.61 | 13.4 | 304.8 |
| 35 | 6  | 9  | 11 | 0.72 | 19.2 | 511.5 |
| 36 | 6  | 8  | 11 | 0.72 | 15.4 | 356.5 |
| 37 | 6  | 9  | 12 | 0.66 | 13.1 | 303.9 |

As noted previously, several of the nonwoven webs of the above Samples were subjected to stretching in the CD to break open the melt stabilized areas thereby creating apertures. And as noted previously, for those nonwoven webs which comprise stripes which were oriented in the MD, the CD stretching modified the Composition element width. Data provided in Table 9 discusses the modification of the Composition element width.

TABLE 9

| Aperture Pattern | Print Width (mm) | Gap (mm) | Ratio | Actual Print Width (mm) | Actual Gap (mm) | Actual Ratio | % Spreading |
|---|---|---|---|---|---|---|---|
| 1 | 0.5 | 1 | 2 | No discernible pattern | | | |
| 1 | 0.5 | 2 | 4 | 1.4 | 2.0 | 1.4 | 185 |
| 1 | 1   | 1 | 1 | No discernible pattern | | | |
| 1 | 1   | 2 | 2 | 2.8 | 1.6 | 0.6 | 176 |
| 1 | 1   | 4 | 4 | 2.4 | 5.0 | 2.1 | 143 |
| 1 | 2   | 2 | 1 | 3.9 | 1.7 | 0.4 | 96  |
| 1 | 2   | 4 | 2 | 4.2 | 4.6 | 1.1 | 109 |
| 2 | 0.5 | 1 | 2 | No discernible pattern | | | |
| 2 | 0.5 | 2 | 4 | 1.4 | 1.7 | 1.2 | 186 |
| 2 | 1   | 1 | 1 | No discernible pattern | | | |
| 2 | 1   | 2 | 2 | 2.3 | 2.1 | 0.9 | 127 |
| 2 | 1   | 4 | 4 | 2.5 | 4.0 | 1.6 | 149 |
| 2 | 2   | 2 | 1 | 3.5 | 1.7 | 0.5 | 76  |
| 2 | 2   | 4 | 2 | 3.7 | 4.1 | 1.1 | 85  |
| 3 | 0.5 | 1 | 2 | No discernible pattern | | | |
| 3 | 0.5 | 2 | 4 | 1.6 | 1.8 | 1.1 | 225 |
| 3 | 1   | 1 | 1 | No discernible pattern | | | |
| 3 | 1   | 2 | 2 | 2.4 | 1.7 | 0.7 | 138 |
| 3 | 1   | 4 | 4 | 2.6 | 4.8 | 1.9 | 155 |
| 3 | 2   | 2 | 1 | 3.8 | 2.0 | 0.5 | 89  |
| 3 | 2   | 4 | 2 | 3.9 | 4.7 | 1.2 | 96  |

TABLE 9-continued

| Aperture Pattern | Print Width (mm) | Gap (mm) | Ratio | Actual Print Width (mm) | Actual Gap (mm) | Actual Ratio | % Spreading |
|---|---|---|---|---|---|---|---|
| none | 0.5 | 0.5 | 1 | No discernible pattern | | | |
| none | 0.5 | 1 | 2 | 1.1 | 0.7 | 0.6 | 122 |
| none | 0.5 | 2 | 4 | 1.3 | 1.5 | 1.2 | 153 |
| none | 0.5 | 4 | 8 | 1.1 | 3.6 | 3.2 | 122 |
| none | 1 | 1 | 1 | 1.7 | 0.7 | 0.4 | 67 |
| none | 1 | 2 | 2 | 1.7 | 1.6 | 0.9 | 67 |
| none | 1 | 4 | 4 | 1.7 | 3.3 | 2.0 | 69 |
| none | 2 | 2 | 1 | 2.8 | 1.3 | 0.5 | 40 |
| none | 2 | 4 | 2 | 2.8 | 3.3 | 1.2 | 42 |
| none | 2 | 8 | 4 | 3.0 | 7.1 | 2.4 | 51 |
| none | 4 | 2 | 0.5 | 4.9 | 1.4 | 0.3 | 22 |
| none | 4 | 4 | 1 | 5.0 | 3.3 | 0.7 | 25 |
| none | 4 | 8 | 2 | 5.3 | 7.0 | 1.3 | 32 |

As shown in Table 9, for those samples having a small compositional element width, e.g. 0.5 mm or 1 mm, and a small spacing between compositions elements, e.g. 0.5 mm or 1 mm, no discernable pattern was recognized by the analysis. It is worth noting that the data provided in Table 9 may be utilized to determine element width and spacing where composition migrates over time in conjunction with or independent of migration via stretching of the web.

In reviewing the data collectively, the inventors have surprisingly discovered that the performance of the samples varied with a ratio of spacing to widths—namely, the ratio of composition element spacing to composition element width. For example, regardless of the orientation of the composition elements, regardless of aperture pattern or whether there were apertures at all, where the ratio of composition element spacing to composition element width was less than about 8, the acquisition speed for the samples improved. Where the ratio was less than about 4, the acquisition speed improved. Where the ratio was greater than about 2, rewet improved as did stain masking. So, taking into account acquisition speed, rewet, and stain masking, the pre-stretching ratio of composition stripe spacing to composition stripe width should be between about 2 to about 8, or between about 2.5 to about 7.5, between about 2.75 to about 6, between about 3 to about 5, between about 3.5 to about 4.5, specifically including any numbers within these ranges and any ranges created thereby. The post-stretching and/or post migration ratio as provided in Table 9, can be greater than about 0.5, greater than about 0.7, greater than about 1.1, greater than about 1.4, greater than about 1.7, greater than about 1.9, greater than about 2.1 and less than about 8, including any values within these ranges or any ranges created thereby. In one particular form, the ratio of composition element spacing to composition element width may be between 0.5 to about 3.0, between about 0.6 and 2.6, or between about 0.7 and 2.3, specifically including all values within these ranges and any ranges created thereby.

The pre-stretch element width 120 may vary from about 0.25 mm to about 2 mm, or between about 0.5 mm to about 1.5 mm, or any values within these ranges or any ranges created thereby. Additionally, the element spacing 130 may be between about 0.5 mm to about 8 mm, 1 mm to about 7 mm, or 2 mm to about 6 mm, 3 mm to about 4 mm, or any values within these ranges or any ranges created thereby. The post-stretch and/or post migration element width may be greater than about 1.4 mm, greater than about 1.6, greater than about 1.8, greater than about 2.0 mm, greater than about 2.3 mm, greater than about 2.5 mm, greater than about 3.0 mm, greater than about 3.5 mm, greater than about 4.0 mm, greater than about 4.2 mm, and less than about 5 mm, specifically including any values within these ranges and any ranges created thereby. In one particular form, the element width may be between 1 mm and about 4 mm, specifically including all values within this range and any range created thereby.

Figure 3A:
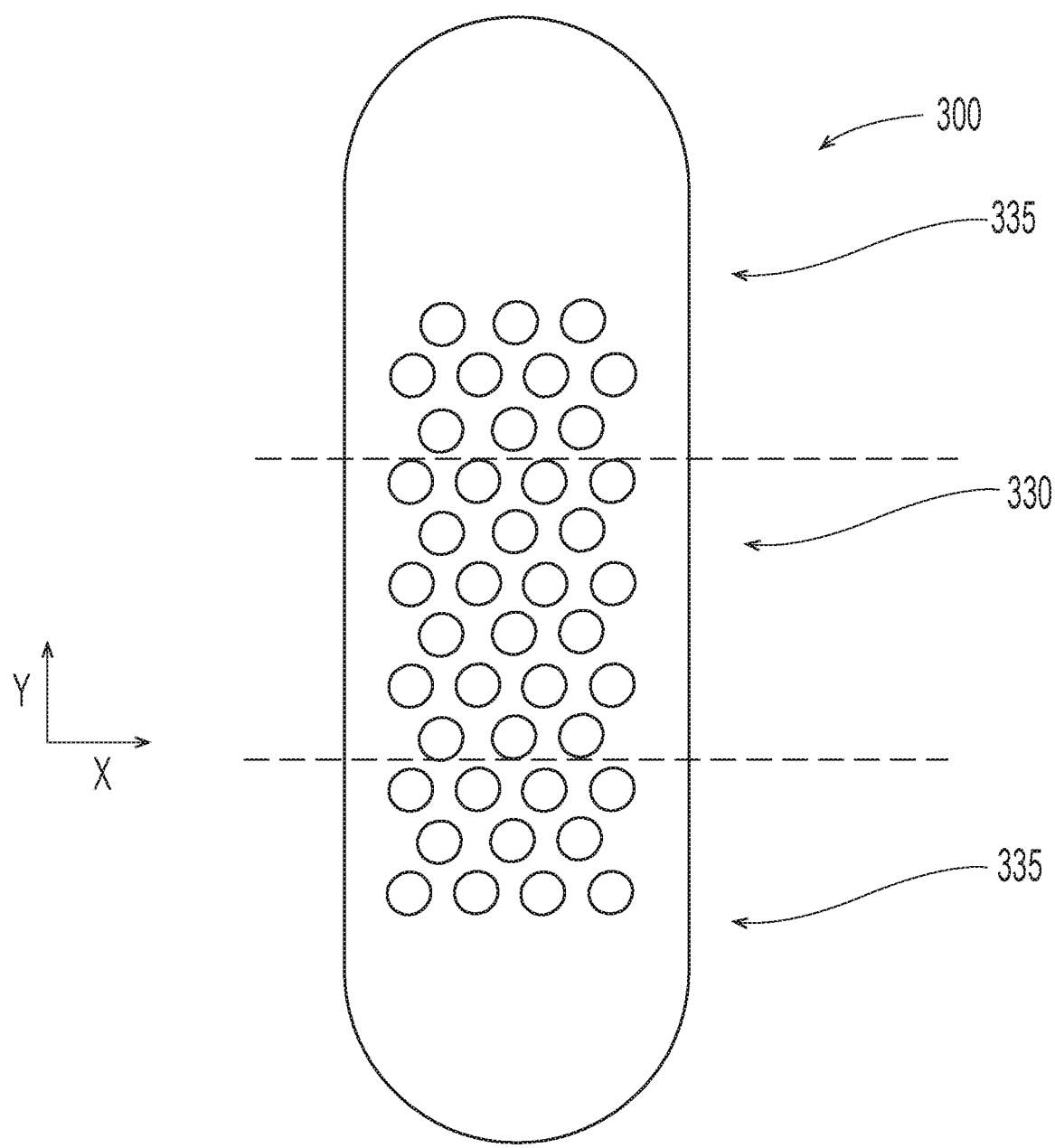
FIGS. 3A-3B are schematic illustrations showing absorbent articles in accordance with the present disclosure.
Figure 3B:
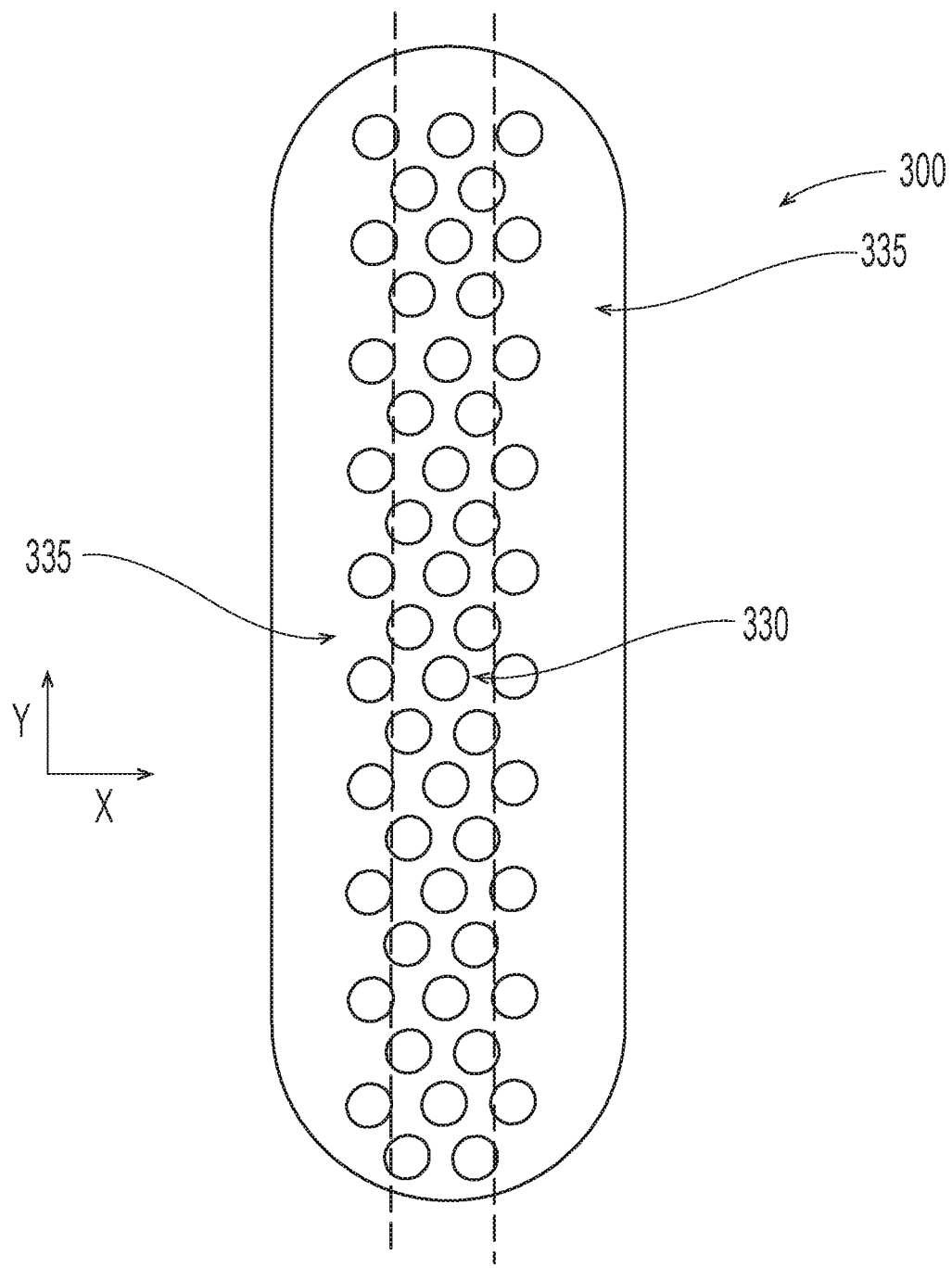

In some forms, it may be beneficial to provide the composition elements in zones. For example, composition element width and/or composition element spacing may be a first value within a first zone and a second different value in outer zones. Some exemplary first zones 330 and outer zones 335 are shown in FIGS. 3A and 3B on a feminine pad 300 for ease of visualization. Note that the size of the apertures has been exaggerated for ease of visualization as well. The absorbent article 300 is shown having an overall longitudinal length generally parallel to a Y-axis and an overall lateral width generally parallel to an X-axis. The absorbent article 300 further comprises a thickness in a Z-direction (not shown) which is perpendicular to an X-Y plane created by the X and Y axes.

As shown, the first zone 330 along with the outer zones 335 may extend the full length of the feminine pad 300. For such arrangements, the first zone 330 may comprise between about 20 percent to about 60 percent of the width of the feminine pad. The outer zones 335 may each comprise between about 14 percent to about 40 percent of the width of the feminine pad 300. And where the feminine pad 300 comprises wings, the wings may be comprised by outer zones 335. As noted previously, the composition element spacing in the first zone 330 may be different than the composition element spacing in the outer zones 335. Alternatively, or in conjunction therewith, the composition element width in the first zone 330 may be different than the composition element width in the outer zones 335.

The first zone 330 is not required to extend the full length of the feminine pad 300. In such arrangements, the first zone 330 may extend the full width of the feminine pad 300 and the outer zones 335 may comprise the ends of the feminine pad 300 and may be disposed on either side of the first zone 330. In such arrangements, the first zone 330 may comprise a target zone. The target zone generally corresponds to the region of intended fluid entry for the feminine pad 300. For menstrual pads, the intended region of fluid entry may be the location on the menstrual pad that corresponds to the vaginal opening. For adult incontinence articles, the intended region of fluid entry may be the location of the incontinence article that corresponds to the urethra or the vulva region as labial tissue can obscure the pathway from the urethra to the absorbent article. And, in general, the target zone may correspond to a portion of the feminine pad 300 that is positioned between the thighs of the wearer during use. The target zone may comprise a transverse centerline (generally parallel to the X-axis) and/or the longitudinal centerline (generally parallel to the Y-axis) of the feminine pad 300. For example, the target zone may be asymmetrically disposed about the transverse centerline, e.g. disposed on one side of the transverse centerline or disposed more on one side of the transverse centerline than the other side of the transverse centerline. A method for determining the extent of the target zone is disclosed hereafter, i.e. Target Zone test method.

Where the first zone does not extend the full length of the feminine pad 300, the first zone and/or target zone may have any suitable length. For example, the first zone and/or target zone may extend a distance greater than or equal to about 15 percent of the total length of the article, greater than or equal to about 20 percent of the total length of the article, greater than or equal to about 30 percent of the total length of the article, greater than or equal to about 40 percent of the total length of the article, greater than or equal to about 50 percent of the total length of the article, greater than about 60 percent of the total length of the article, greater than about 70 percent of the total length of the article, or greater than about 80 percent of the total length of the article, specifically including all values within these ranges and any ranges created thereby. The width of the target zone may be 100 percent of the width of the article, less than 90 percent, less than 80 percent, less than 70 percent, less than 60 percent, less than 50 percent, less than 40 percent, less than 30 percent, or less than 20 percent, specifically including all values within these ranges and any ranges created thereby.

Where the target zone does not comprise 100 percent of the width of the article, outboard of the target zone, composition may be applied having ratios that are different than the ratios of the composition elements within the target zone.

Where articles comprise a target zone 300, compositional elements disposed within the target zone may have a ratio of composition element spacing to composition element width of (assuming pre-stretch or no CD stretch) between about 2 to about 8, or between about 2.5 to about 7.5, or between about 2.75 to about 6, or between about 3 to about 5 or between about 3.5 to about 4.5, specifically including any numbers within these ranges and any ranges created thereby. Post stretching and/or migration, the ratio of composition element spacing to composition element width may be greater than about 0.5, greater than about 0.7, greater than about 1.1, greater than about 1.4, greater than about 1.7, greater than about 1.9, greater than about 2.1 and less than about 8, including any values within these ranges or any ranges created thereby. In one particular form, the ratio of composition element spacing to composition element width may be between 0.5 to about 3.0, between about 0.6 and 2.6, or between about 0.7 and 2.3, specifically including all values within these ranges and any ranges created thereby.

Outside of the target zone 330, i.e. in the outer zones 335 can comprise a ratio of composition element spacing to composition element width which are more effective for masking. For example, the ratio pre-stretch or no stretch may be greater than about 4, greater than about 6, greater than about 8, greater than about 12, greater than about 16, greater than about 20, greater than about 30, greater than about 40, or greater than about 50, specifically including any values within these ranges and any ranges created thereby. As another example, post-stretching and/or migration, the ratio of composition element spacing to composition element width can be greater than 1.1, greater than 1.4, greater than about 1.6, greater than about 1.9, greater than about 2.1, greater than about 3, greater than about 5, or greater than about 8, specifically including all values within these ranges and any ranges created thereby.

Still in other forms, the outer zones 335 may be sans composition elements. In one particular form, the ratio of composition element spacing to composition element width may be between 0.6 to about 15, between about 2.0 and 10, or between about 3.0 and 8, specifically including all values within these ranges and any ranges created thereby. Where wings are comprised by the absorbent articles described herein, the wings may be provided with no composition treatment. Or, the wings may be provided with minimal treatment.

Processing

Compositions may be applied to the absorbent articles of the present invention via any suitable manner. In some forms, the compositions may be printed onto a topsheet of the article. For example, as shown in FIG. 4A, a printer 460 may be disposed between a first unit operation 440 and a second unit operation 450. The first unit operation 440 may comprise a pair of rolls 442 and 444 which compress a precursor web 410 thereby forming a plurality of melt stabilized areas as described heretofore thereby forming a plurality of intermediate features in an intermediate web 415. The second unit operation 450 may comprise a pair of intermeshing rolls 452 and 454 which then stretch the intermediate web 415 breaking apart melt stabilized areas in the intermediate web 415 thereby forming apertures in a final web 480.

In the configuration of FIG. 4A, the printer 460 may deposit composition elements onto the intermediate web 415 with the composition width and composition spacing desired. Or, the printer 460 may print composition onto the intermediate web 415 with the variability described herein regarding first zones 330 and/or target zones (See FIGS. 3A-3B) and outer zones 335 (See FIGS. 3A-3B). The printer 460 can deposit the composition elements onto the intermediate web 415 in the MD or CD direction.

In some forms, an absorbent article manufacturer may obtain the intermediate web 415 from a web supplier. In such forms, the printer 460 may deposit composition as described herein onto the intermediate web 415 without having to execute the first unit operation as shown in FIG. 4A.

Another exemplary arrangement is shown in FIG. 4B. As shown, the printer 460 may be positioned downstream of the second unit operation 450. In such forms, the printer 460 may deposit composition onto the final web 480 with the desired composition element width and composition element spacing. Or, the printer 460 may print composition onto the final web 480 with the variability described herein regarding first zones 330 and/or target zones (See FIGS. 3A-3B) and outer zones 335 (See FIGS. 3A-3B). The printer 460 can deposit the composition elements onto the final web 480 in the MD or CD direction.

The configuration of FIG. 4B may be utilized where both the first unit operation 440 and second unit operation 450 are present. This configuration may also be utilized where the first unit operation 440 is not present. For example, where an absorbent article manufacturer obtains a web comprising a plurality of melt stabilized areas from a web manufacturer, the need for the first unit operation 440 may be absent. Similarly, alternative aperturing processes for which only one unit operation is needed, e.g. hot pin, punching, cutting, slitting, etc., are known in the art. If such operations are utilized, the arrangement shown in FIG. 4B may be utilized.

Another exemplary arrangement is shown in FIG. 4C. As shown, the printer 460 may be positioned upstream of the first unit operation 440. In such forms, the printer 460 may deposit composition onto the precursor web 410 with the desired composition element width and composition element spacing. Or, the printer 460 may print composition onto the precursor web 410 with the variability described herein regarding first zones 330 and/or target zones (See FIGS. 3A-3B) and outer zones 335 (See FIGS. 3A-3B). The printer 460 can deposit the composition elements onto the precursor web 410 in the MD or CD direction.

Similar to the configuration of FIG. 4B, the configuration shown in FIG. 4C may be utilized where both the first unit operation 440 and second unit operation 450 are present. This configuration may also be utilized where the first unit operation 440 is not present. For example, where an absorbent article manufacturer obtains a web comprising a plurality of melt stabilized areas from a web manufacturer, the need for the first unit operation 440 may be absent. Similarly, alternative aperturing processes for which only one unit operation is needed, e.g. hot pin, punching, cutting, slitting, etc., are known in the art. If such operations are utilized, the arrangement shown in FIG. 4C may be utilized.

Precursor Web

As discussed previously, the precursor web may comprise a single layer or multiple layers of material. For example, the precursor webs of the present disclosure may comprise a nonwoven or laminates thereof. The precursor web may comprise any suitable material. Some suitable examples include nonwovens, wovens, cellulosic materials, elastic materials, non-elastic materials, high-loft materials, and/or foams. The precursor webs may also comprise one or more layers of one or more nonwoven materials, combinations of different nonwoven materials, combinations of one or more nonwoven materials, or combinations of one or more different materials, for example. Precursor webs having one or more layers of the same or similar materials are also within the scope of the present disclosure.

As another example, the precursor web may comprise a layer comprising a plurality of substrates. For example, the precursor web may comprise a spunbonded nonwoven as a layer. The spunbonded nonwoven may comprise a plurality of substrates which can be integrally formed with one another. For example, substrates may be produced via a spunbond process. A first substrate may be produced by a first spin beam and a second substrate may be produced via a second spin beam. Additional substrates may be produced via additional spin beams on the same spunbond manufacturing line.

Precursor webs may comprise any suitable material. For example, precursor web materials may comprise PE/PP bi-component fiber spunbond webs. Other suitable precursor webs may comprise spunbond webs comprising side-by-side crimped fibers (e.g. PE/PP or PP/PP) that are bonded via calendar (thermal point) bonding or through-air bonding. For those configurations with multiple layers a first layer and second layer of the patterned apertured web of the present invention may comprise a crimped spunbond layer. For these configurations, the crimped spunbond layers may be combined from roll stock and joined as provided herein. However, where the precursor web comprises a first substrate and a second substrate, each may be crimped spunbond substrates formed on a spunbond manufacturing line where the first substrate is formed from a first spin beam while the second substrate is formed from a second spin beam.

Other suitable precursor webs may comprise carded staple fibers comprising polypropylene, polyethylene terephthalate, polyethylene/polypropylene bi-component, polyethylene/polyethylene terephthalate bi-component, or the like, which are calendar bonded, through-air bonded, resin bonded or hydroentangled. The precursor webs may comprise microfibers and/or nanofibers, optionally with other fibers. In some circumstances, multiple layer webs may be desired over a single layer webs (even at the same basis weight) due to increased uniformity/opacity and the ability to combine webs having different properties. For example, an extensible spunbond nonwoven carrier layer may be combined with a soft, crimped fiber nonwoven (spunbond or carded). The substrates may have the same or different surface energy, for example, the top layer may be hydrophobic and the lower layer may be hydrophilic. The layers may have different permeability/capillarity, e.g. the upper layer may have higher permeability and the lower layer have higher capillarity in order to set up a capillary gradient and aid in moving fluid away from the surface (or topsheet) of an absorbent article and into an absorbent core of the absorbent article.

Additionally, the precursor webs may comprise a surface treatment and/or additive to the constituent material of the precursor web. For example, the precursor web may comprise a hydrophobic melt additive. For such webs, a composition applied in a composition site may be hydrophilic. One particularly suitable melt additive is glycerol tristearate. Additional suitable melt additives and surface treatments of materials is discussed in additional detail in U.S. Pat. Nos. 8,178,748, 8,026,188; 4,578,414; 5,969,026; U.S Patent Application Publication Nos. 2012/0100772; 2014/0272261; 2012/0296036; 2014/0087941; U.S. patent application Ser. Nos. 14/849,630; 13/833,390; European Patent No. 2411061; and PCT Patent Application Publication No. 2012/162130.

The inventors have surprisingly found that the addition of some surfactants to a phobically treated web—via surface treatment or melt additive—can reduce the migration of the surfactant. Additional detail regarding this discovery, among other features, is provided in U.S. Application Ser. No. 62/689,909, entitled ABSORBENT ARTICLE WITH TOPSHEET TREATED TO REDUCE SURFACTANT MIGRATION.

Compositions

For those forms where a hydrophilic composition is applied to the precursor web, intermediate web or final web, any suitable hydrophilic composition may be utilized. Some suitable examples of hydrophilic compositions include a surfactant or combination of surfactants with hydrophilic/lyophilic balance number (HLB) of greater than or equal to about 7, more desirably greater than or equal to about 10, and even more desirably, a HLB of greater than or equal to about 14. Hydrophilic agents that do not generally have a measured HLB may also be used.

Some suitable examples of hydrophilic compositions include non-ionic surfactants including esters, amides, carboxylic acids, alcohols, ethers—polyoxyethylene, polyoxypropylene, sorbitan, ethoxylated fatty alcohols, alyl phenol polyethoxylates, lecithin, glycerol esters and their ethoxylates, and sugar based surfactants (polysorbates, polyglycosides). Other suitable nonionic surfactants include: ethoxylates, including fatty acid ester ethoxylates, fatty acid ether ethoxylates, and ethoxylated sugar derivatives (e.g., ethoxylated fatty acid polyesters, ethoxylated fatty acid sorbitan esters, and the like), and the like, as well as combinations comprising at least one of the foregoing. Other suitable examples include anionic surfactants including sulfonates, sulfates, phosphates, alkali metal salts of fatty acids, fatty alcohol monoesters of sulfuric acid, linear alkyl benzene sulfonates, alkyl diphenyloxide sulfonates, lignin sulfonates, olefin sulfonates, sulfosuccinates, and sulfated ethoxylates of fatty alcohols. Other suitable examples include cationic surfactants including amines (primary, secondary, tertiary), quaternary ammoniums, pyridinium, quaternary ammonium salts-QUATS, alkylated pyridinium salts, alkyl primary, secondary, tertiary amines, and alkanolamides. Other suitable examples include zwiterionic surfactants including amino acids and derivatives, amine oxide, betaines, and alkyl amine oxides. Other suitable examples include polymeric surfactants including polyamines, carboxylic acid polymers and copolymers, EO/PO block copolymers, ethylene oxide polymers and copolymers, and polyvinylpyrrolidone. Other suitable examples include silicone surfactants including dimethyl siloxane polymers with hydrophile.

And other suitable examples include perfluorocarboxylic acid salts and fluorosurfactants.

The hydrophilic agents that do not generally have a measured HLB may also be used. Such hydrophilic agents may include, without limitation, diols, such as glycols and polyglycols. Suitable nonionic surfactants include, but are not intended to be limited to, C2-8 diols and polyglycols, and the like. Generally, the diol may be glycols (C2 and C3 diols) and polyglycols. The term "polyglycol" refers to a dihydroxy ether formed by dehydration of two or more glycol molecules. A representative, non-limiting list of useful polyglycols, includes: ethylene glycol, propylene glycol, polyethylene glycols, polypropylene glycols, methoxypolyethylene glycols, polybutylene glycols, block copolymers of butylene oxide and ethylene oxide, and the like, as well as combinations comprising at least one of the foregoing.

Additionally, suitable philic composition include finishing treatments which are typically proprietary blends of synthetic surfactant solutions which are commercially available. Examples include materials from Schill & Seilacher AG under the tradename Silastol (e.g. Silastol PHP 26, Silastol PHP 90, Silastol PST-N, Silastol PHP 207, Silastol PHP 28 & Silastol PHP 8), from Pulcra Chemicals under the tradename Stantex® (e.g. Stantex S 6327, Stantex S 6087-4, & Stantex PP 602), among others.

Where the precursor webs comprise hydrophilic constituent material, the composition applied may be hydrophobic. In such instances, any suitable hydrophobic composition may be utilized. Some suitable examples of hydrophobic compositions include fluorinated or perfluorinated polymers; silicones; fluorochemicals; zirconium compounds; oils; latexes; waxes; crosslinking resins; and blends thereof; fluorochemical urethanes, ureas, esters, ethers, alcohols, epoxides, allophanates, amides, amines (and salts thereof), acids (and salts thereof), carbodiimides, guanidines, oxazolidinones, isocyanurates, and biurets; nanostructured particles selected from fumed silica, hydrophobic titania, zinc oxide, nanoclay, and mixtures thereof; fats and oils, glycerol derivatives; hydrophobic silicones or suitable combinations thereof.

Examples of suitable silicone polymers are selected from the group consisting of silicone MQ resins, polydimethysiloxanes, crosslinked silicones, silicone liquid elastomers, and combinations thereof. Polydimethylsiloxanes can be selected from the group consisting of vinyl-terminated polydimethsiloxanes, methyl hydrogen dimethylsiloxanes, hydroxyl-terminated polydimethysiloxanes, organo-modified polydimethylsiloxanes, and combinations thereof, among others.

Other hydrophobic materials suitable for the present invention are well defined and documented in the art. For example, US patent application 2002/0064639 describes hydrophobic compositions selected from the group consisting of silicones, fluorochemicals, zirconium compounds, oils, latexes, waxes, crosslinking resins, and blends thereof. Representative water repellent fluorochemical compounds described in U.S. Pat. No. 7,407,899 include fluorochemical urethanes, ureas, esters, ethers, alcohols, epoxides, allophanates, amides, amines (and salts thereof), acids (and salts thereof), carbodiimides, guanidines, oxazolidinones, isocyanurates, and biurets. U.S. Pat. No. 6,548,732 describes hydrophobic substances from the group consisting of theobroma oil, cacao butter, cocoa butter, petrolatum, mineral jelly, white mineral oil, dimethicone, zinc oxide preparation, chinese white, zinc white, beeswax, lanolin, jojoba oil and combinations thereof. Additionally, U.S. Pat. No. 9,364,859, discusses substrates that exhibit superhydrophobic properties when treated with a composition comprising a hydrophobic component selected from fluorinated polymers, perfluorinated polymers, and mixtures thereof; nano-structured particles selected from fumed silica, hydrophobic titania, zinc oxide, nanoclay, and mixtures thereof; and water for an overall water-based, non-organic solvent. Examples of such compositions and surfaces in U.S. Pat. No. 9,364,859, exemplify the superhydrophobic treated surfaces that may be used as the nonwoven topsheet of the present invention.

Additionally, waxes and other hydrophobic materials can be used, including petroleum-based emollients; fatty acid esters; polyol polyesters; fatty alcohol ethers; sterols and sterol esters, and their derivatives; triglycerides; glyceryl esters; ceramides; and mixtures thereof. The fatty acids may originate from vegetable, animal, and/or synthetic sources. Some fatty acids may range from a C8 fatty acid to a C30 fatty acid, or from a C12 fatty acid to a C22 fatty acid. In another embodiment, a substantially saturated fatty acid may be used, particularly when saturation arises as a result of hydrogenation of fatty acid precursor. Examples of fatty acid derivatives include fatty alcohols, fatty acid esters, and fatty acid amides.

Suitable fatty alcohols (R—OH) include those derived from C12-C28 fatty acids.

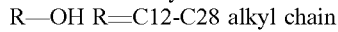

R—OH R=C12-C28 alkyl chain

Suitable fatty acid esters include those fatty acid esters derived from a mixture of C12-C28 fatty acids and short chain (C1-C8, preferably C1-C3) monohydric alcohols preferably from a mixture of C12-C22 saturated fatty acids and short chain (C1-C8, preferably C1-C3) monohydric alcohols. The hydrophobic melt additive may comprise a mixture of mono, di, and/or tri-fatty acid esters. An example includes fatty acid ester with glycerol as the backbone.

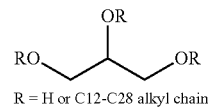

R = H or C12-C28 alkyl chain

The glycerol derived fatty acid ester has at least one alkyl chain, at least two, or three chains to a glycerol, to form a mono, di, or triglyceride. Suitable examples of triglycerides include glycerol thibehenate (C22), glycerol tristearate (C18), glycerol tripalmitate (C16), and glycerol trimyristate (C14), and mixtures thereof. In the case of triglycerides and diglycerides, the alkyl chains could be the same length, or different length. Example includes a triglyceride with one alkyl C18 chain and two C16 alkyl chain, or two C18 alkyl chains and one C16 chain. Preferred triglycerides include alkyl chains derived from C14-C22 fatty acids.

Suitable fatty acid amides include those derives from a mixture of C12-C28 fatty acids (saturated or unsaturated) and primary or secondary amines A suitable example of a primary fatty acid amide includes those derived from a fatty acid and ammonia.

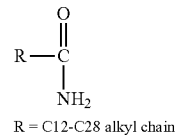

R = C12-C28 alkyl chain

Suitable examples include erucamide, oleamide and behanamide. Other suitable hydrophobic melt additives include hydrophobic silicones, ethoxylated fatty alcohols.

Additionally, in some forms, in conjunction with the hydrophilic compositions or independent therefrom, compositions applied may comprise a lotion. Such deposition is believed to reduce the likelihood of rewet. Additionally, the lotions may provide skin benefits as described herein.

Any suitable lotion may be utilized as a composition of the present invention. Some suitable lotions are described in U.S. Patent Application Publication Nos. 2003/0206943 and 2007/0219515. Lotions suitable for use as compositions in the present invention may comprise from about 60-99.9 percent of a carrier. Suitable carrier compounds include petroleum-based hydrocarbons having from about 8 to about 32 carbon atoms, fatty alcohols having from about 12 to about 18 carbon atoms, polysiloxane compounds, fatty acid esters, alkyl ethoxylates, lower alcohols having from about 2 to about 6 carbon atoms, low molecular weight glycols and polyols, fatty alcohol ethers having from about 12 to about 22 carbon atoms in their fatty chain, lanolin and its derivatives, ethylene glycol derivatives of $C_{12}$-$C_{22}$ fatty acids, glyceride and its derivatives including acetoglycerides and ethoxylated glycerides of $C_{12}$-$C_{15}$ fatty acids, and mixtures thereof. Other suitable carriers include oils or fats, such as natural oils or fats, or natural oil or fat derivatives, in particular of plant or animal origin. Suitable carriers further encompass waxes. As used herein, the term 'wax' refers to oil soluble materials that have a waxy constituency and have a melting point or range of above ambient temperature, in particular above 25° C. Waxes are materials that have a solid to semi-solid (creamy) consistency, crystalline or not, being of relative low viscosity a little above their liquefying point. Suitable waxes which can be incorporated into the lotion composition include animal, vegetable, mineral or silicone based waxes which may be natural or synthetic, and including mixtures thereof.

Additionally, lotions suitable for use with the present invention may comprise optional ingredients such as skin treatment agents including hexamidine, zinc oxide, and niacinamide, glycerine, chamomile, panthenol, fats and oils, and/or skin conditioning agents, perfumes, deodorants, opacifiers, astringents, preservatives, emulsifying agents, film formers, stabilizers, proteins, lecithin, urea, colloidal oatmeal, pH control agents. Additional optional ingredients include particles, wetting agents, and/or viscosity or thickening agents.

Depending on the manner in which the compositions are provided to the web, it is important to consider the rheology of the compositions being applied. For example, viscosity of the composition can be an important factor as viscosities which are too low can migrate out of the applied area, e.g. first composition sites. In contrast, a composition with too high of a viscosity can be difficult to apply via digital printer. And, other forms of application of the composition may prove to be much slower than that of the digital printer.

The compositions of the present disclosure may be formulated to optimize its deposition by non-contact printing, e.g. ink jet printing. For example, the components of the desired composition can be dissolved or dispersed in a suitable solvent, such as water or another organic solvent. Some suitable organic solvents include ketones such as acetone, diethyl ketone, cyclohexanone and the like. Additional suitable solvents include alcohols such as methanol, ethanol, n-propanol, isopropanol, n-butanol, 1-methoxy-2-propanol, and the like. Additional suitable solvents include esters such as ethyl acetate, propyl acetate, butyl acetate and the like. Additional examples include ethers, lactones and amides. If desired, a mixture of solvents may be used. Additionally, surfactants, rheology modifiers, and colorants such as dyes or pigments may be added to the formulation.

Inkjet printing generally relies on the generation and disposition of sequences of droplets onto a substrate. Behavior of the composition during droplet ejection is dependent on material properties such as density, viscosity and surface tension. The behavior of a composition when inkjet printed can be predicted via two dimensionless numbers, i.e. Ohnesorge number and Weber number. The equation for determining the Oh number is provided below.

$$Oh = \frac{\eta}{\sqrt{\rho \gamma L}}$$

where η is viscosity, ρ is density, γ is surface tension of the composition, and L is the characteristic diameter (print head nozzle diameter for inkjet printing in meters).

Stable drop formation can be characterized by the reciprocal of the Ohnesorge number, namely Z=1/Oh. Stable drop formation can be expected from compositions when 14≥Z≥1. The viscosity of the desired composition should be measured at target operating temperature with shear rates between 200 and 20 s-1. The surface tension should be recorded in N/m. The density should be calculated in kg/m3, and the viscosity should be recorded in Pa·s.

Additionally, a composition of the present invention may comprise a Weber number of between about 4 and 1000. The Weber number may be calculated as follows:

$$We = \frac{v^2 \rho L}{\gamma}$$

where ρ is the density of the composition in kg/m3; v is the velocity of the composition in m/s; L is the characteristic diameter (print head nozzle diameter for inkjet printing; and γ is the surface tension in N/m.

The compositions of the present disclosure may comprise a viscosity of between about 5 and 25 centipoise. The compositions may comprise a surface tension of between about 25 and 40 dyne/cm. In some forms of the present invention, the compositions may comprise a density of from about 0.6 grams/cubic cm to about 2.0 grams/cubic cm, specifically including all values within this range and any ranges created thereby.

In addition to ink jet, several contact methods can be used to apply the compositions of the present disclosure onto a web. Other methods may be used to add the composition to the web including flexographic printing, spray, slot coating, and the like. Where printing is desired, useful compositions are those which are liquid at 70 degrees Celsius or greater and stable at high temperature. Such compositions may be applied pure without the use of solvents or at least a reduced amount of solvents. For example, Stantex 56327 may be added under these conditions with the use of solvents by printing. Some additional examples of hydrophilic compositions include Stantex S6327 and Stantex 56887 (from Pulcra). These hydrophilic compositions are nonionic surfactants which when heated, have reduced viscosity to such an extent that the composition is printable via phase changing material ink jet printing.

Similarly, hydrophobic compositions, such as fatty acid esters, triglycerides (GTS-glycerol tristearate, GTM—glycerol trimyrstate, and others.), waxes (petrolatum, soy wax), fatty alcohols, petrolatum, and the like may be printed. Mixtures of these components are also printable, e.g. printed lotion–petrolatum+fatty alcohol. Some of these materials are solids at room temperature and when heated, have a viscosity which is amenable to printing.

Equipment

Any suitable printer may be utilized with the present invention. As noted previously, the composition sites may comprise a plurality of discrete dots or droplets. The volume of the ink droplets can depend on the particular printing technology. By way of example, printing units that are VIDEOJET™ continuous ink jet printers can have ink drop volumes of about 240 pL and are delivered at relatively high drop velocities (e.g., about 13 m/s). Other printing technology (e.g. piezo drop on demand) can deliver ink drops having relatively small volumes, such as ink drops having a volume ranging from about 1 pL to about 24 pL and believed to be as high as about 80 pL in some forms. These drops are delivered at lower drop velocities (i.e., about ½ m/s) than continuous inkjet printing. Those skilled in the art know there are different inkjet technologies (e.g., continuous, piezo, thermal, valve) and different drop size ranges and different jet velocities. In general, smaller drop size infers that the CD dpi (resolution) is higher. The range 1-24 pL would equate to a CD resolution of 300-600 dpi. The VIDEOJET CD resolution is 128 dpi. So, more drops in CD can mean better opportunity to hit a fiber, which can result in better image quality and less ink blow-though. The slower the drop speed, the less ink blow-through.

An exemplary continuous ink jet printer is available from Videojet™ sold under the trade name of Videojet BX™. For the continuous ink jet printer, the ink droplets are dispensed from all of the jets of the print heads continuously, but only certain ink droplets are allowed to reach the precursor web, intermediate web, or secondary web, at the composition sites. The other ink droplets can be prevented from reaching the precursor web, intermediate web, or secondary web by deflecting the ink droplets into a recycling flow for a continuous re-use. The operation of the individual ink jets of each print head can be controlled by a controller included in the Videojet BX™ system.

Another suitable printer is the Galaxy Phase Change online Printer available from FujiFilm. Print heads for the Galaxy Phase Change online printer are available from Fujifilm Dimatix under the trade name Galaxy PH256/80HM. The advantage of using a heated print head, is that viscous liquids can be printed if the viscosity is reduced as temperature increases.

Disposable Absorbent Articles

Figure 5:
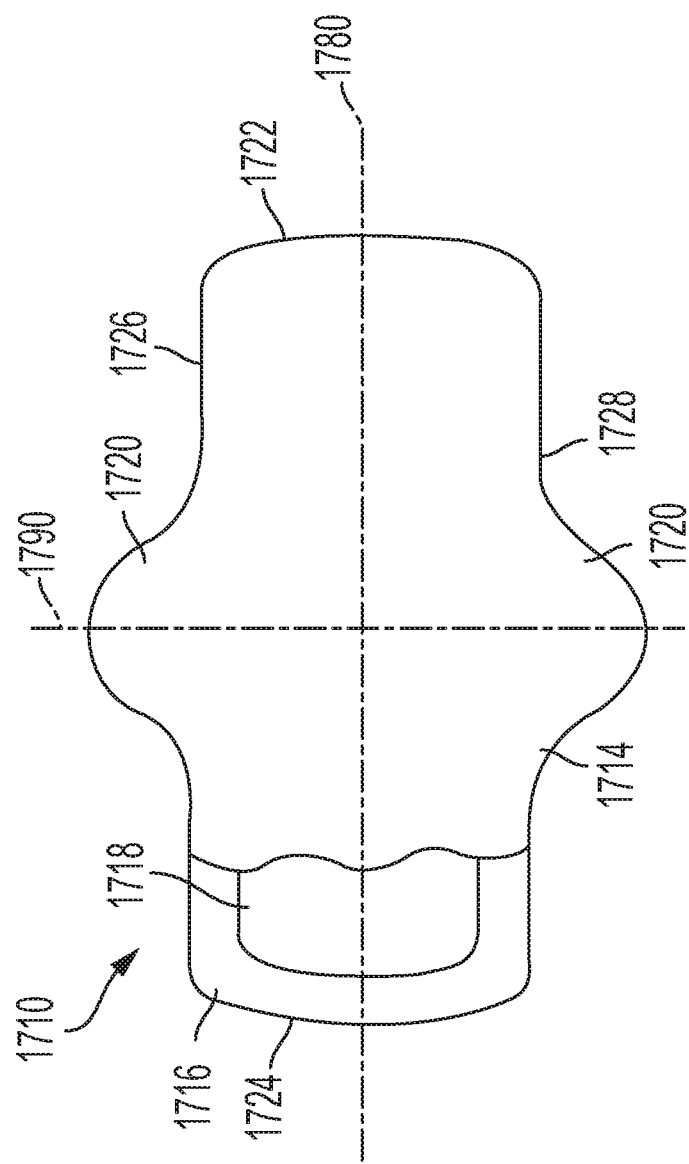
FIG. 5 is a schematic illustration showing a sanitary pad in accordance with the present disclosure.

The composition elements described herein may be utilized with any suitable absorbent article. Some exemplary absorbent articles are described hereafter. Referring to FIG. 5, an absorbent article 1710 which may utilize the material webs described herein may be a sanitary napkin/feminine hygiene pad. As shown, the sanitary napkin 1710 may comprise a liquid permeable topsheet 1714, a liquid impermeable, or substantially liquid impermeable, backsheet 1716, and an absorbent core 1718 positioned intermediate the topsheet 1714 and the backsheet 1716. The sanitary napkin 1710 may comprise wings 1720 extending outwardly with respect to a longitudinal axis 1780 of the sanitary napkin 1710. The sanitary napkin 1710 may also comprise a lateral axis 1790. The wings 1720 may be joined to the topsheet 1714, the backsheet 1716, and/or the absorbent core 1718. The sanitary napkin 1710 may also comprise a front edge 1722, a rear edge 1724 longitudinally opposing the front edge 1722, a first side edge 1726, and a second side edge 1728 laterally opposing the first side edge 1726. The longitudinal axis 1780 may extend from a midpoint of the front edge 1722 to a midpoint of the rear edge 1724. The lateral axis 1790 may extend from a midpoint of the first side edge 1726 to a midpoint of the second side edge 1728. The sanitary napkin 1710 may also be provided with additional features commonly found in sanitary napkins as is known in the art. In some forms of the present invention, the wings may be provided with zones of extensibility as described in U.S. Pat. No. 5,972,806.

Any suitable absorbent core known in the art may be utilized. The absorbent core 1718 may be any absorbent member which is generally compressible, conformable, non-irritating to the wearer's skin, and capable of absorbing and retaining liquids such as urine, menses, and/or other body exudates. The absorbent core 1718 may be manufactured from a wide variety of liquid-absorbent materials commonly used in disposable absorbent articles such as comminuted wood pulp which is generally referred to as airfelt. The absorbent core 1718 may comprise superabsorbent polymers (SAP) and less than 15%, less than 10%, less than 5%, less than 3%, or less than 1% of airfelt, or be completely free of airfelt. Examples of other suitable absorbent materials comprise creped cellulose wadding, meltblown polymers including coform, chemically stiffened, modified or cross-linked cellulosic fibers, tissue including tissue wraps and tissue laminates, absorbent foams, absorbent sponges, superabsorbent polymers, absorbent gelling materials, or any equivalent material or combinations of materials.

The configuration and construction of the absorbent core 1718 may vary (e.g., the absorbent core may have varying caliper zones, a hydrophilic gradient, a superabsorbent gradient, or lower average density and lower average basis weight acquisition zones; or may comprise one or more layers or structures). In some forms, the absorbent core 1718 may comprise one or more channels, such as two, three, four, five, or six channels.

The absorbent core 1718 of the present disclosure may comprise one or more adhesives, for example, to help immobilize the SAP or other absorbent materials within a core wrap and/or to ensure integrity of the core wrap, in particular when the core wrap is made of two or more substrates. The core wrap may extend to a larger area than required for containing the absorbent material(s) within.

Absorbent cores comprising relatively high amounts of SAP with various core designs are disclosed in U.S. Pat. No. 5,599,335 to Goldman et al., EP 1,447,066 to Busam et al., WO 95/11652 to Tanzer et al., U.S. Pat. Publ. No. 2008/0312622A1 to Hundorf et al., and WO 2012/052172 to Van Malderen.

Other forms and more details regarding channels and pockets that are free of, or substantially free of absorbent materials, such as SAP, within absorbent cores are discussed in greater detail in U.S. Patent Application Publication Nos. 2014/0163500, 2014/0163506, and 2014/0163511, all published on Jun. 12, 2014.

The absorbent article 1710 may comprise additional layers between the topsheet 1714 and the absorbent core 1718. For example, the absorbent article 1710 may comprise a secondary topsheet and/or an acquisition layer positioned between the topsheet 1714 and the absorbent core 1718.

The backsheet can comprise a liquid impervious film. The backsheet can be impervious to liquids (e.g., body fluids) and can be typically manufactured from a thin plastic film.

However, typically the backsheet can permit vapours to escape from the disposable article. In an embodiment, a microporous polyethylene film can be used for the backsheet. A suitable microporous polyethylene film is manufactured by Mitsui Toatsu Chemicals, Inc., Nagoya, Japan and marketed in the trade as PG-P.

One suitable material for the backsheet can be a liquid impervious thermoplastic film having a thickness of from about 0.012 mm (0.50 mil) to about 0.051 mm (2.0 mils), for example including polyethylene or polypropylene. Typically, the backsheet can have a basis weight of from about 5 $g/m^2$ to about 35 $g/m^2$. However, it should be noted that other flexible liquid impervious materials may be used as the backsheet. Herein, "flexible" refers to materials which are compliant and which will readily conform to the general shape and contours of the wearers body.

The backsheet can be typically positioned adjacent an outer-facing surface of the absorbent core and can be joined thereto by any suitable attachment device known in the art. For example, the backsheet may be secured to the absorbent core by a uniform continuous layer of adhesive, a patterned layer of adhesive, or an array of separate lines, spirals, or spots of adhesive. Illustrative, but non-limiting adhesives, include adhesives manufactured by H. B. Fuller Company of St. Paul, Minn., U.S.A., and marketed as HL-1358J. An example of a suitable attachment device including an open pattern network of filaments of adhesive is disclosed in U.S. Pat. No. 4,573,986 entitled "Disposable Waste-Containment Garment", which issued to Minetola et al. on Mar. 4, 1986. Another suitable attachment device including several lines of adhesive filaments swirled into a spiral pattern is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Alternatively, the attachment device may include heat bonds, thermal fusion bonds, pressure bonds, ultrasonic bonds, dynamic mechanical bonds, or any other suitable attachment device or combinations of these attachment devices. The backsheet may be additionally secured to the topsheet by any of the above-cited attachment devices/methods.

Still another example of a disposable absorbent article which may utilize the material webs of the present invention are diapers which include non-refastenable pants, re-fastenable pants and/or re-fastenable diapers. Diapers have can have a similar construction to that of sanitary napkins. An exemplary diaper is described below.

Figure 6:
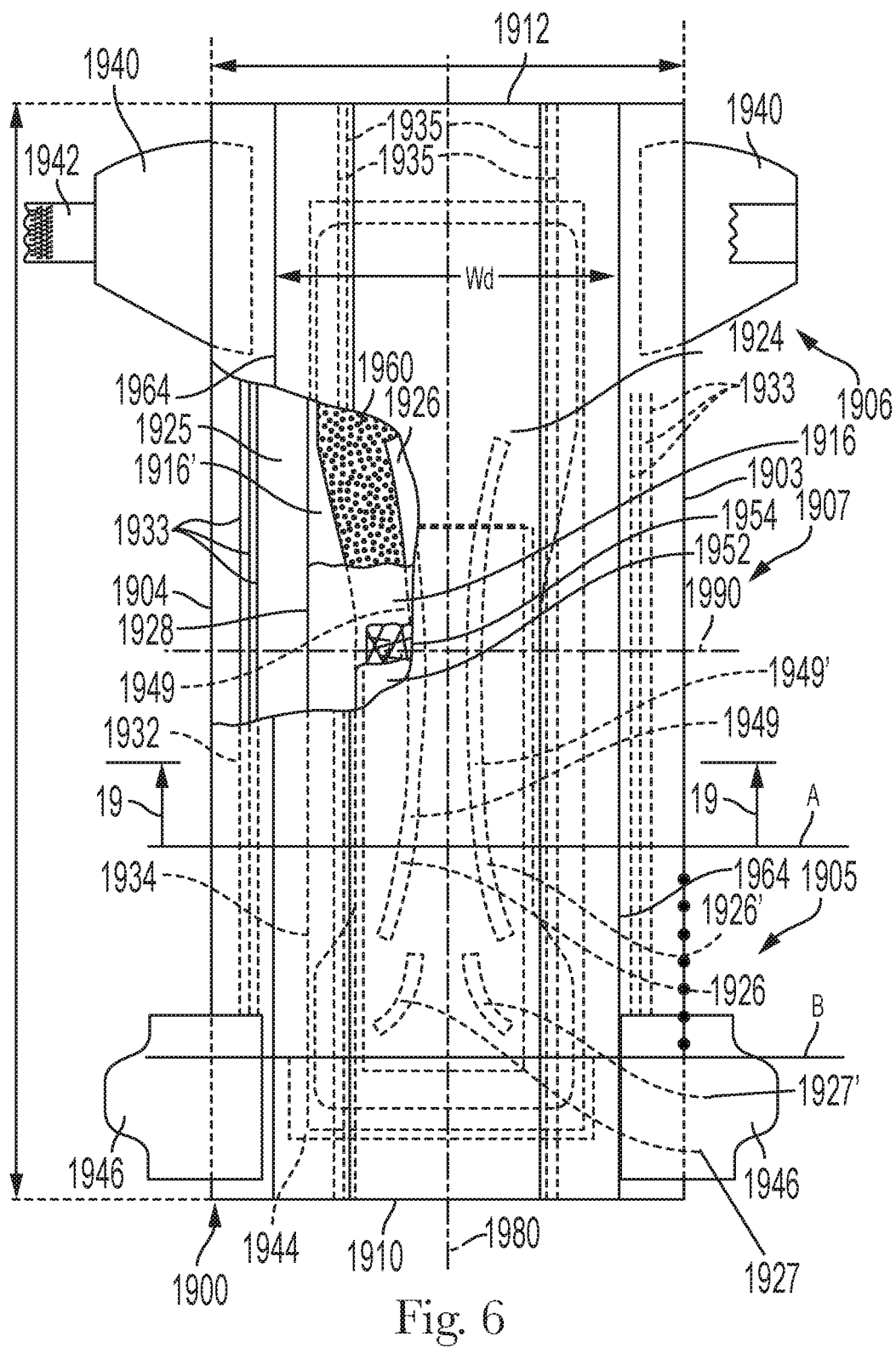
FIG. 6 is a schematic illustration showing a diaper in accordance with the present disclosure.

Referring to FIG. 6, a plan view of an example absorbent article that is a diaper 1900 in its flat-out, uncontracted state (i.e., with elastic induced contraction pulled out) with portions of the structure being cut-away to more clearly show the construction of the diaper 1900 and with its wearer-facing surface toward the viewer. This diaper is shown for illustration purpose only as the present disclosure may be used for making a wide variety of diapers and other absorbent articles.

The absorbent article may comprise a liquid permeable topsheet 1924, a liquid impermeable backsheet 1925, an absorbent core 1928 positioned at least partially intermediate the topsheet 1924 and the backsheet 1925, and barrier leg cuffs 1934. The absorbent article may also comprise a liquid management system ("LMS") 1950 (shown in FIG. 7), which, in the example represented, comprises a distribution layer 1954 and an acquisition layer 1952 that will both be further discussed below. In various forms, the acquisition layer 1952 may instead distribute bodily exudates and the distribution layer 1954 may instead acquire bodily exudates or both layers may distribute and/or acquire bodily exudates. The LMS 1950 may also be provided as a single layer or two or more layers. The absorbent article may also comprise elasticized gasketing cuffs 1932 joined to the chassis of the absorbent article, typically via the topsheet and/or backsheet, and substantially planar with the chassis of the diaper.

The Figures also show typical taped diaper components such as a fastening system comprising adhesive tabs 1942 or other mechanical fasteners attached towards the rear edge of the absorbent article 1900 and cooperating with a landing zone on the front of the absorbent article 1900. The absorbent article may also comprise other typical elements, which are not represented, such as a rear elastic waist feature and a front elastic waist feature, for example.

The absorbent article 1900 may comprise a front waist edge 1910, a rear waist edge 1912 longitudinally opposing the front waist edge 1910, a first side edge 1903, and a second side edge 1904 laterally opposing the first side edge 1903. The front waist edge 1910 is the edge of the absorbent article 1900 which is intended to be placed towards the front of the user when worn, and the rear waist edge 1912 is the opposite edge. Together the front waist edge 1910 and the rear waist edge form waist opening when the absorbent article 1900 is donned on a wearer. The absorbent article 1900 may have a longitudinal axis 1980 extending from the lateral midpoint of the front waist edge 1910 to a lateral midpoint of the rear waist edge 1912 of the absorbent article 1900 and dividing the absorbent article 1900 in two substantially symmetrical halves relative to the longitudinal axis 1980, with article placed flat and viewed from the wearer-facing surface as illustrated FIG. 19. The absorbent article may also have a lateral axis 1990 extending from the longitudinal midpoint of the first side edge 1903 to the longitudinal midpoint of the second side edge 1904. The length L of the absorbent article 1900 may be measured along the longitudinal axis 1980 from the front waist edge 1910 to the rear waist edge 1912. The crotch width of the absorbent article 1900 may be measured along the lateral axis 1990 from the first side edge 1903 to the second side edge 1904. The absorbent article 1900 may comprise a front waist region 1905, a rear waist region 1906, and a crotch region 1907. The front waist region, the rear waist region, and the crotch region each define ⅓ of the longitudinal length of the absorbent article. Front and back portions may also be defined on opposite sides of the lateral axis 1990.

The topsheet 1924, the backsheet 1925, the absorbent core 1928, and the other article components may be assembled in a variety of configurations, in particular by gluing or heat embossing, for example. Example diaper configurations are described generally in U.S. Pat. Nos. 3,860,003, 5,221,274, 5,554,145, 5,569,234, 5,580,411, and 6,004,306.

The absorbent core 1928 may comprise an absorbent material comprising 75% to 100%, at least 80%, at least 85%, at least 90%, at least 95%, or at least 99%, all by weight, of the absorbent material, specifically reciting all 0.1% increments within the above-specified ranges and all ranges formed therein or thereby, and a core wrap enclosing the absorbent material. The core wrap may typically comprise two materials, substrates, or nonwoven materials 16 and 16' for the top side and bottom side of the core.

Figure 7:
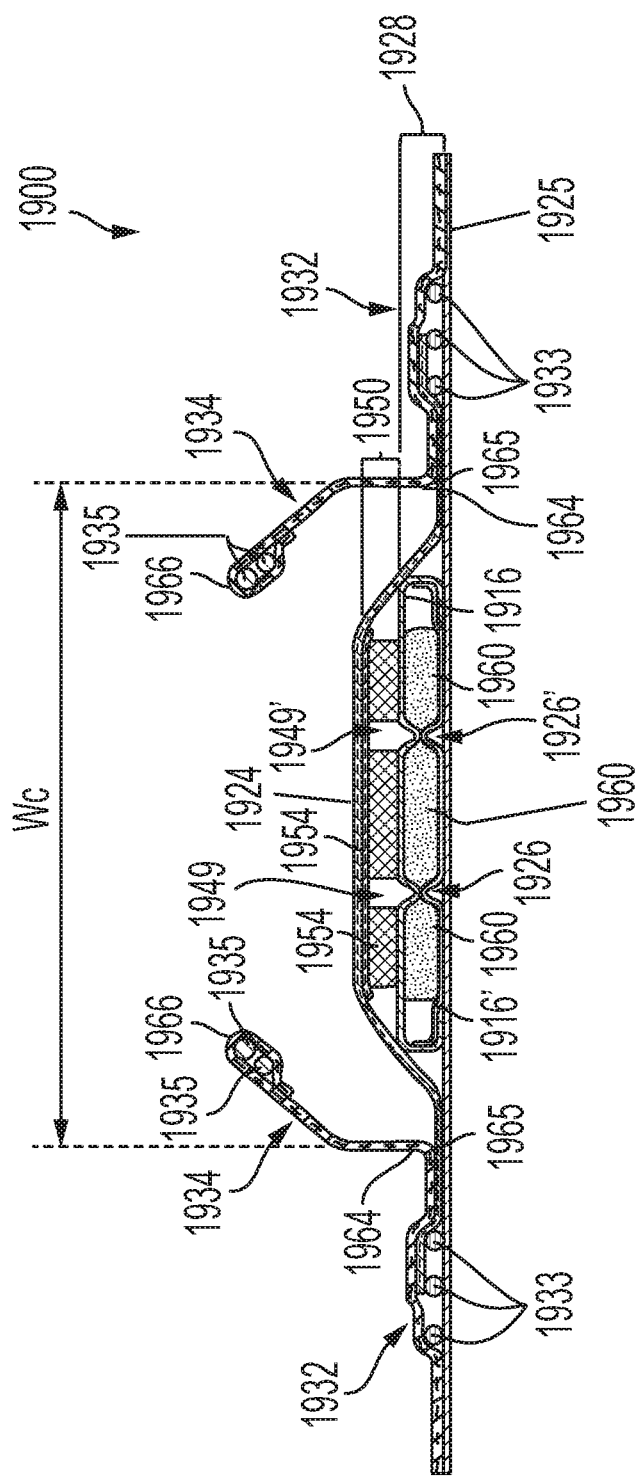
FIG. 7 is a cross section of the diaper of FIG. 6 taken along line 19-19.

The absorbent core 1928 may comprises one or more channels, represented in FIGS. 7 and 8, as the four channels 1926, 1926' and 1927, 1927'. Additionally or alternatively, the LMS 1950 may comprises one or more channels, represented in FIGS. 5-7 as channels 1949, 1949'. In some forms, the channels of the LMS 1950 may be positioned within the absorbent article 1900 such they aligned with, substantially aligned with, overlap, or at least partially overlap, the channels of the absorbent core 1928. These and other components of the absorbent articles will now be discussed in more details.

The topsheet 1924 is the part of the absorbent article that is directly in contact with the wearer's skin. The topsheet 1924 may be joined to the backsheet 1925, the core 1928 and/or any other layers as is known to those of skill in the art. Usually, the topsheet 1924 and the backsheet 1925 are joined directly to each other in some locations (e.g., on or close to the periphery of the article) and are indirectly joined together in other locations by directly joining them to one or more other elements of the absorbent article 1900.

The backsheet 1925 is generally that portion of the absorbent article 1900 positioned adjacent the garment-facing surface of the absorbent core 1928 and which prevents, or at least inhibits, the bodily exudates absorbed and contained therein from soiling articles such as bedsheets and undergarments. The backsheet 1925 is typically impermeable, or at least substantially impermeable, to liquids (e.g., urine, running BM), but permeable to vapors to allow the diaper to "breath". The backsheet may, for example, be or comprise a thin plastic film such as a thermoplastic film having a thickness of about 0.012 mm to about 0.051 mm Example backsheet films include those manufactured by Tredegar Corporation, based in Richmond, Va., and sold under the trade name CPC2 film. Other suitable backsheet materials may include breathable materials which permit vapors to escape from the absorbent article 1900 while still preventing, or at least inhibiting, bodily exudates from passing through the backsheet 1925. Example breathable materials may include materials such as woven webs, nonwoven webs, and composite materials such as film-coated nonwoven webs, microporous films, and monolithic films.

The backsheet 1925 may be joined to the topsheet 1924, the absorbent core 1928, and/or any other element of the absorbent article 1900 by any attachment methods known to those of skill in the art. Suitable attachment methods are described above with respect to methods for joining the topsheet 1924 to other elements of the absorbent article 1900.

As used herein, the term "absorbent core" refers to the individual component of the absorbent article having the most absorbent capacity and that comprises an absorbent material. The absorbent core may comprise a core wrap or core bag (hereafter "core wrap") enclosing the absorbent material. The term "absorbent core" does not include the LMS or any other component of the absorbent article which is not either integral part of the core wrap or placed within the core wrap. The absorbent core may comprise, consist essentially of, or consist of, a core wrap, absorbent material as defined below, and glue enclosed within the core wrap. Pulp or air-felt may also be present within the core wrap and may form a portion of the absorbent material. The absorbent core periphery, which may be the periphery of the core wrap, may define any suitable shape, such as a "T," "Y," "hour-glass," or "dog-bone" shape, for example. An absorbent core periphery having a generally "dog bone" or "hour-glass" shape may taper along its width towards the middle or "crotch" region of the core. In this way, the absorbent core may have a relatively narrow width in an area of the absorbent core intended to be placed in the crotch region of an absorbent article.

The absorbent core 1928 of the present disclosure may comprise an absorbent material with a high amount of superabsorbent polymers (herein abbreviated as "SAP") enclosed within a core wrap. The SAP content may represent 70% to 100% or at least 70%, 75%, 80%, 85%, 90%, 95%, 99%, or 100% by weight of the absorbent material contained in the core wrap. The SAP useful with the present disclosure may include a variety of water-insoluble, but water-swellable polymers capable of absorbing large quantities of fluids. The core wrap is not considered as absorbent material for the purpose of assessing the percentage of SAP in the absorbent core. The remainder of the absorbent material in the core 1928 may be air-felt.

"Absorbent material" means a material which has some absorbency property or liquid retaining properties, such as SAP, cellulosic fibers as well as synthetic fibers. Typically, glues used in making absorbent cores have no absorbency properties and are not considered as absorbent material. The SAP content may be higher than 80%, for example at least 85%, at least 90%, at least 95%, at least 99%, and even up to and including 100% of the weight of the absorbent material contained within the core wrap, as stated above. This provides a relatively thin core compared to conventional cores typically comprising between 40-60% SAP, for example, and high content of cellulose fibers or airfelt. The absorbent material may comprise less than 15% or less than 10% weight percent of natural or synthetic fibers, less than 5% weight percent, less than 3% weight percent, less than 2% weight percent, less than 1% weight percent, or may even be substantially free of, or free of, natural and/or synthetic fibers, specifically reciting all 0.1% increments within the specified ranges and all ranges formed therein or thereby. The absorbent material may comprise little or no airfelt (cellulose) fibers, in particular the absorbent core may comprise less than 15%, 10%, 5%, 3%, 2%, 1% airfelt (cellulose) fibers by weight, or may even be substantially free of, or free of, cellulose fibers, specifically reciting all 0.1% increments within the specified ranges and all ranges formed therein or thereby.

The absorbent core 1928 may also comprise a generally planar top side and a generally planar bottom side. The core 1928 may have a longitudinal axis 80' corresponding substantially to the longitudinal axis 80 of the absorbent article, as seen from the top in a planar view as in FIG. 19. The absorbent material may be distributed in higher amount towards the front side than towards the rear side as more absorbency may be required at the front in particular articles. The absorbent material may have a non-uniform basis weight or a uniform basis weight across any portion of the core. The core wrap may be formed by two nonwoven materials, substrates, laminates, or other materials, 1916, 1916' which may be at least partially sealed along the sides of the absorbent core. The core wrap may be at least partially sealed along its front side, rear side, and two longitudinal sides so that substantially no absorbent material leaks out of the absorbent core wrap. The first material, substrate, or nonwoven 1916 may at least partially surround the second material, substrate, or nonwoven 1916' to form the core wrap. The first material 1916 may surround a portion of the second material 1916' proximate to the first and second side edges 1903 and 1904.

Cores comprising relatively high amount of SAP with various core designs are disclosed in U.S. Pat. No. 5,599,335 (Goldman), EP 1,447,066 (Busam), WO 95/11652 (Tanzer), U.S. Pat. Publ. No. 2008/0312622A1 (Hundorf), and WO 2012/052172 (Van Malderen).

The absorbent material may be one or more continuous layers present within the core wrap. Alternatively, the absorbent material may be comprised of individual pockets or stripes of absorbent material enclosed within the core wrap.

In the first case, the absorbent material may be, for example, obtained by the application of a single continuous layer of absorbent material. The continuous layer of absorbent material, in particular of SAP, may also be obtained by combining two or more absorbent layers having discontinuous absorbent material application pattern, wherein the resulting layer is substantially continuously distributed across the absorbent particulate polymer material area, as disclosed in U.S. Pat. Appl. Publ. No. 2008/0312622A1 (Hundorf), for example. The absorbent core 1928 may comprise a first absorbent layer and a second absorbent layer. The first absorbent layer may comprise the first material 1916 and a first layer of absorbent material 1960, which may be 100% or less of SAP. The second absorbent layer may comprise the second material 1916' and a second layer of absorbent material 1960, which may also be 100% or less of SAP.

The fibrous thermoplastic adhesive material may be at least partially in contact with the absorbent material 1960 in the land areas and at least partially in contact with the materials 1916 and 1916' in the junction areas. This imparts an essentially three-dimensional structure to the fibrous layer of thermoplastic adhesive material, which in itself is essentially a two-dimensional structure of relatively small thickness, as compared to the dimension in length and width directions. Thereby, the fibrous thermoplastic adhesive material may provide cavities to cover the absorbent material in the land area, and thereby immobilizes this absorbent material, which may be 100% or less of SAP.

The core wrap may be made of a single substrate, material, or nonwoven folded around the absorbent material, or may comprise two (or more) substrates, materials, or nonwovens which are attached to another. Typical attachments are the so-called C-wrap and/or sandwich wrap. In a C-wrap, the longitudinal and/or transversal edges of one of the substrates are folded over the other substrate to form flaps. These flaps are then bonded to the external surface of the other substrate, typically by gluing. Other techniques may be used to form a core wrap. For example, the longitudinal and/or transversal edges of the substrates may be bonded together and then folded underneath the absorbent core 1928 and bonded in that position.

The core wrap may be at least partially sealed along all the sides of the absorbent core so that substantially no absorbent material leaks out of the core. By "substantially no absorbent material" it is meant that less than 5%, less than 2%, less than 1%, or about 0% by weight of absorbent material escape the core wrap. The term "seal" is to be understood in a broad sense. The seal does not need to be continuous along the whole periphery of the core wrap but may be discontinuous along part or the whole of it, such as formed by a series of seal points spaced on a line. A seal may be formed by gluing and/or thermal bonding.

The core wrap may also be formed by a single substrate which may enclose as in a parcel wrap the absorbent material and be sealed along the front side and rear side of the core and one longitudinal seal.

The absorbent article 1900 may comprise a pair of barrier leg cuffs 1934. Each barrier leg cuff may be formed by a piece of material which is bonded to the absorbent article so it can extend upwards from the inner surface of the absorbent article and provide improved containment of liquids and other bodily exudates approximately at the junction of the torso and legs of the wearer. The barrier leg cuffs 1934 are delimited by a proximal edge 1964 joined directly or indirectly to the topsheet 1924 and/or the backsheet 1925 and a free terminal edge 1966, which is intended to contact and form a seal with the wearer's skin. The barrier leg cuffs 1934 extend at least partially between the front waist edge 1910 and the rear waist edge 1912 of the absorbent article on opposite sides of the longitudinal axis 1980 and are at least present in the crotch region 1907. The barrier leg cuffs 1934 may be joined at the proximal edge 1964 with the chassis of the absorbent article by a bond 1965 which may be made by gluing, fusion bonding, or combination of other suitable bonding processes. The bond 1965 at the proximal edge 64 may be continuous or intermittent. The bond 1965 closest to the raised section of the leg cuffs 1934 delimits the proximal edge 1964 of the standing up section of the leg cuffs 1934.

The barrier leg cuffs 1934 may be integral with the topsheet 1924 or the backsheet 1925 or may be a separate material joined to the absorbent article's chassis. The material of the barrier leg cuffs 1934 may extend through the whole length of the diapers but may be "tack bonded" to the topsheet 1924 towards the front waist edge 1910 and rear waist edge 1912 of the absorbent article so that in these sections the barrier leg cuff material remains flush with the topsheet 1924.

Each barrier leg cuff 1934 may comprise one, two or more elastic strands or strips of film 1935 close to this free terminal edge 1966 to provide a better seal.

In addition to the barrier leg cuffs 1934, the absorbent article may comprise gasketing cuffs 1932, which are joined to the chassis of the absorbent article, in particular to the topsheet 1924 and/or the backsheet 1925 and are placed externally relative to the barrier leg cuffs 1934. The gasketing cuffs 1932 may provide a better seal around the thighs of the wearer. Each gasketing leg cuff may comprise one or more elastic strings 1933 or elastic elements in the chassis of the absorbent article between the topsheet 1924 and backsheet 1925 in the area of the leg openings. All or a portion of the barrier leg and/or gasketing cuffs may be treated with a lotion or skin care composition. The barrier leg cuffs may be constructed in a number of different configurations, including those described in U.S. Pat. App. Publ. No. 2012/0277713.

In a form, the absorbent article may comprise front ears 1946 and rear ears 1940. The ears may be an integral part of the chassis, such as formed from the topsheet 1924 and/or backsheet 1925 as side panel. Alternatively, as represented on FIG. 19, the ears (1946, 1940) may be separate elements attached by gluing, heat embossing, and/or pressure bonding. The rear ears 1940 may be stretchable to facilitate the attachment of the tabs 1942 to the landing zone 1944 and maintain the taped diapers in place around the wearer's waist. The rear ears 1940 may also be elastic or extensible to provide a more comfortable and contouring fit by initially conformably fitting the absorbent article to the wearer and sustaining this fit throughout the time of wear well past when absorbent article has been loaded with exudates since the elasticized ears allow the sides of the absorbent article to expand and contract.

One function of the LMS 1950 is to quickly acquire the fluid and distribute it to the absorbent core 1928 in an efficient manner. The LMS 1950 may comprise one or more layers, which may form a unitary layer or may remain as discrete layers which may be attached to each other. The LMS 1950 may comprise two layers: a distribution layer 1954 and an acquisition layer 1952 disposed between the absorbent core and the topsheet, but the present disclosure is not limited to such a configuration.

The LMS 1950 may comprise SAP as this may slow the acquisition and distribution of the fluid. In other forms, the LMS may be substantially free (e.g., 80%, 85%, 90%, 95%, or 99% free of) or completely free of SAP. The LMS may also comprise one or more of a variety of other suitable types of materials, such as opened-cell foam, air-laid fibers, or carded, resin bonded nonwoven materials, for example. Suitable example LMSs are described in WO 2000/59430 (Daley), WO 95/10996 (Richards), U.S. Pat. No. 5,700,254 (McDowall), and WO 02/067809 (Grad), for example.

The LMS 1950 may comprise a distribution layer 1954. The distribution layer 1954 may comprise at least 50% or more by weight of cross-linked cellulose fibers, for example. The cross-linked cellulosic fibers may be crimped, twisted, or curled, or a combination thereof including crimped, twisted, and curled. This type of material is disclosed in U.S. Pat. Publ. No. 2008/0312622 A1 (Hundorf).

The LMS 1950 may alternatively or additionally comprise an acquisition layer 1952. The acquisition layer 1952 may be disposed, for example, between the distribution layer 1954 and the topsheet 1924. The acquisition layer 1952 may be or may comprise a non-woven material, such as an SMS or SMMS material, comprising a spunbonded, a melt-blown and a further spunbonded layer or alternatively a carded chemical-bonded nonwoven. The acquisition layer 1952 may comprise air or wet-laid cellulosic, cross-linked cellulosic, or synthetic fibers, or blends thereof. The acquisition layer 1952 may comprise a roll-stock web of synthetic fibers (which may be processed to increase void space, such as by solid state formation), or a combination of synthetic and cellulosic fibers, bonded together to form a highloft material. Alternatively, the acquisition layer 1952 may comprise absorbent open cell foam. The nonwoven material may be latex bonded.

The LMS 1950 of the absorbent article 1900 may comprise channels that may generally enable better conformation of the absorbent article to the wearer's anatomy, leading to increased freedom-of-movement and reduced gapping. One or more of the channels of the LMS 1950 may be configured to work in concert with various channels in the absorbent core 1928, as discussed above. Furthermore, channels in the LMS 1950 may also provide increased void space to hold and distribute urine, BM or other bodily exudates within the absorbent article, leading to reduced leakage and skin contact Channels in the LMS 1950 may also provide internal serviceable indicia, especially when highlighted via physical differences in texture, color, and/or pattern, to facilitate achieving the correct alignment of the absorbent article on a wearer. Thus, such physical differences may be, for example, visually and/or tactilely noticeable.

As stated previously, the material webs of the present disclosure may be utilized as a topsheet for a disposable absorbent article, examples of which include the sanitary napkin 1710 and diaper 1900 discussed heretofore.

The material webs of the present disclosure may be used as components of absorbent articles. More than one material web may be used in a single absorbent article. In such a context, the material webs may form at least a portion of: a topsheet; a topsheet and an acquisition layer; a topsheet and a distribution layer; an acquisition layer and a distribution layer; a topsheet, an acquisition layer, and a distribution layer; an outer cover; a backsheet; an outer cover and a backsheet, wherein a film (non-apertured layer) forms the backsheet and a nonwoven web forms the outer cover; a leg cuff; an ear or side panel; a fastener; a waist band; belt or any other suitable portion of an absorbent article. The number of strata in a nonwoven web may also be determined by the nonwoven laminates' particular use.

In some forms, additional layers may be positioned between the topsheet and the absorbent core. For example, a secondary topsheet, acquisition layer, and/or distribution layer, each of which are known in the art, may be positioned between the topsheet and the absorbent core of the absorbent article.

Product Arrays

As noted previously, the provision of composition elements to absorbent articles can span a large number of different absorbent articles. For example, feminine sanitary pads, liners, adult incontinence pads, adult incontinence pants, baby diapers, diaper pants, and the like. However, the average amount of fluid insult can vary greatly from product to product. For example, the amount of liquid insult that may occur for a pantiliner is typically much less than what is expected for a baby diaper or for an adult incontinence product. However, with the flexibility of the methodology described herein, disposable absorbent products can be modified to provide good acquisition, rewet, and masking benefits as desired.

For example, a product array may include a first absorbent article comprising an arrangement of composition elements as described herein having a first ratio of composition element spacing to composition element width. A second absorbent article may comprise an arrangement of composition elements as described herein having a second ratio of composition element spacing to composition element width. Forms are contemplated where the first value is greater than the second value. For example, the first absorbent article may be a feminine pad, and the first ratio (post stretching and/or post migration) may be about greater than about 0.5, greater than about 0.7, greater than about 1.1, greater than about 1.4, greater than about 1.7, greater than about 1.9, greater than about 2.1 and less than about 8, including any values within these ranges or any ranges created thereby. In contrast, the second absorbent article may be a diaper having lower second ratio (post stretching and/or post migration) than the foregoing first ratio. Forms are contemplated where the first absorbent article and the second absorbent article are the same type of absorbent article, e.g. diapers. However, in such forms, the first absorbent article and the second absorbent article may be different sizes, e.g. size 1 versus size 4.

Forms of the present invention are also contemplated where the composition elements of the first absorbent article and the second absorbent article are applied in a first target zone and a second target zone, respectively, s as described herein. However, in such forms, the first ratio of the first absorbent article in the first target zone may be different than the second ratio of the second absorbent article in its target zone. For example, the first ratio in the first target zone may be greater than the second ratio in the second target zone.

Test Methods

Linear distances may be measured by any appropriate instrument that is calibrated and capable of a measurement to the nearest 0.1 mm Area measurements are made using the projected area of the article, as viewed orthogonally to the plane of the longitudinal and transverse axes, in square millimeters to the nearest 0.1 mm$^2$.

Artificial Menstrual Fluid (AMF) Preparation

The Artificial Menstrual Fluid (AMF) is composed of a mixture of defibrinated sheep blood, a phosphate buffered saline solution and a mucous component. The AMF is prepared such that it has a viscosity between 7.15 to 8.65 centistokes at 23° C.

Viscosity on the AMF is performed using a low viscosity rotary viscometer (a suitable instrument is the Cannon LV-2020 Rotary Viscometer with UL adapter, Cannon Instrument Co., State College, Pa., or equivalent). The appropriate size spindle for the viscosity range is selected, and instrument is operated and calibrated as per the manufacturer. Measurements are taken at 23° C.±1 C.° and at 60 rpm. Results are reported to the nearest 0.01 centistokes.

Reagents needed for the AMF preparation include: defibrinated sheep blood with a packed cell volume of 38% or greater (collected under sterile conditions, available from Cleveland Scientific, Inc., Bath, OH, or equivalent), gastric mucin with a viscosity target of 3-4 centistokes when prepared as a 2% aqueous solution (crude form, available from Sterilized American Laboratories, Inc., Omaha, NE, or equivalent), 10% v/v lactic acid aqueous solution, 10% w/v potassium hydroxide aqueous solution, sodium phosphate dibasic anhydrous (reagent grade), sodium chloride (reagent grade), sodium phosphate monobasic monohydrate (reagent grade) and distilled water, each available from VWR International or equivalent source.

The phosphate buffered saline solution consists of two individually prepared solutions (Solution A and Solution B). To prepare 1 L of Solution A, add 1.38±0.005 g of sodium phosphate monobasic monohydrate and 8.50±0.005 g of sodium chloride to a 1000 mL volumetric flask and add distilled water to volume. Mix thoroughly. To prepare 1 L of Solution B, add 1.42±0.005 g of sodium phosphate dibasic anhydrous and 8.50±0.005 g of sodium chloride to a 1000 mL volumetric flask and add distilled water to volume. Mix thoroughly. To prepare the phosphate buffered saline solution, add 450±10 mL of Solution B to a 1000 mL beaker and stir at low speed on a stir plate. Insert a calibrated pH probe (accurate to 0.1) into the beaker of Solution B and add enough Solution A, while stirring, to bring the pH to 7.2±0.1.

The mucous component is a mixture of the phosphate buffered saline solution, potassium hydroxide aqueous solution, gastric mucin and lactic acid aqueous solution. The amount of gastric mucin added to the mucous component directly affects the final viscosity of the prepared AMF. To determine the amount of gastric mucin needed to achieve AMF within the target viscosity range (7.15-8.65 centistokes at 23° C.) prepare 3 batches of AMF with varying amounts of gastric mucin in the mucous component, and then interpolate the exact amount needed from a concentration versus viscosity curve with a least squares linear fit through the three points. A successful range of gastric mucin is usually between 38 to 50 grams.

To prepare about 500 mL of the mucous component, add 460±10 mL of the previously prepared phosphate buffered saline solution and 7.5±0.5 mL of the 10% w/v potassium hydroxide aqueous solution to a 1000 mL heavy duty glass beaker. Place this beaker onto a stirring hot plate and while stirring, bring the temperature to 45° C.±5 C°. Weigh the pre-determined amount of gastric mucin (±0.50 g) and slowly sprinkle it, without clumping, into the previously prepared liquid that has been brought to 45° C. Cover the beaker and continue mixing. Over a period of 15 minutes bring the temperature of this mixture to above 50° C. but not to exceed 80° C. Continue heating with gentle stirring for 2.5 hours while maintaining this temperature range. After the 2.5 hours has elapsed, remove the beaker from the hot plate and cool to below 40° C. Next add 1.8±0.2 mL of the 10% v/v lactic acid aqueous solution and mix thoroughly. Autoclave the mucous component mixture at 121° C. for 15 minutes and allow 5 minutes for cool down. Remove the mixture of mucous component from the autoclave and stir until the temperature reaches 23° C.±1 C°.

Allow the temperature of the sheep blood and mucous component to come to 23° C.±1 C°. Using a 500 mL graduated cylinder, measure the volume of the entire batch of the previously prepared mucous component and add it to a 1200 mL beaker. Add an equal volume of sheep blood to the beaker and mix thoroughly. Using the viscosity method previously described, ensure the viscosity of the AMF is between 7.15-8.65 centistokes. If not the batch is disposed and another batch is made adjusting the mucous component as appropriate.

The qualified AMF should be refrigerated at 4° C. unless intended for immediate use. AMF may be stored in an air-tight container at 4° C. for up to 48 hours after preparation. Prior to testing, the AMF must be brought to 23° C.±1 C°. Any unused portion is discarded after testing is complete.

Acquisition Time and Rewet Method

Acquisition time is measured for an absorbent article loaded with Artificial Menstrual Fluid (AMF), prepared as described herein. A known volume of AMF is introduced three times, each successive dose starting two minutes after the previous dose has absorbed. The time required for each dose to be absorbed by the article are recorded. Subsequent to the acquisition test, a rewet method is performed to determine the mass of fluid expressed from the article under pressure. Test samples are conditioned at 23° C.±2 C.° and 50%±2% relative humidity for 2 hours prior to testing and all testing is performed under these same environmental conditions.

The confining weight used for the rewet test has a flat level base with a contact surface that is 64±1 mm wide by 83±1 mm and a mass of 2268±2 grams (5 pounds). This weight provides a confining pressure of 4.1 kPa (0.60 psi) on the test article. The rewet substrate is two sheets of filter paper with dimensions 4 inch by 4 inch. A suitable filter paper is Ahlstrom Grade 989 (available from Ahlstrom-Munksjo North America LLC, Alpharetta, GA) or equivalent.

Perform the acquisition test as follows. Remove the test article from its wrapper. If folded, gently unfold and smooth out any wrinkles. Place the test article horizontally flat, with the top sheet of the product facing upward. Position the tip of a mechanical pipette about 1 cm above the center (longitudinal and lateral midpoint) of the article's absorbent core, and accurately pipette 1.00 mL±0.05 mL of AMF onto the surface. The fluid is dispensed without splashing, within a period of 2 seconds. As soon as the fluid makes contact with the test sample, start a timer accurate to 0.01 seconds. After the fluid has been acquired (no pool of fluid left on the surface), stop the timer and record the acquisition time to the nearest 0.01 second. Wait 2 minutes. In like fashion, a second and third dose of AMF are applied to the test sample and the acquisition times are recorded to the nearest 0.01 second. Proceed with the Rewet test 2 minutes after the third dose has been acquired.

Perform the rewet part of the test as follows. Measure the dry mass of two filter papers to the nearest 0.0001 grams and record as Mass$_{Dry}$. Gently place the dry filter papers over the center (longitudinal and lateral midpoint) of the test article's absorbent core. Gently place the base of the confining weight over the center (longitudinal and lateral midpoint) of the filter paper, positioning the length (long side) of the weight parallel to the longitudinal direction of the test article. Immediately start a timer accurate to 0.01 seconds. After 30 seconds, carefully remove the confining weight. Measure the mass of the filter papers to the nearest 0.0001 grams and record as Mass$_{Wet}$. Calculate rewet as the difference between Mass$_{Wet}$ and Mass$_{Dry}$ for the filter papers and record as Rewet Value to the nearest 0.0001 grams.

This entire procedure is repeated on five substantially similar replicate articles. The reported value is the average of the five individual recorded measurements for each Acquisition Time (first, second and third) to the nearest 0.01 second and Rewet Value to the nearest 0.0001 gram.

Stain Perception Measurement Method

Stain perception is measured by the size and color intensity of a fluid stain visible on an absorbent article. Artificial menstrual fluid (AMF), prepared as described herein, is dosed onto the surface of an article, and is photographed under controlled conditions. The photographic image is then calibrated and analyzed using image analysis software to obtain measurements of the size and color intensity of the resulting visible stain. All measurements are performed at constant temperature (23° C.±2 C.°) and relative humidity (50%±2%).

The absorbent article, a calibrated color standard containing 24 standard color chips (e.g., ColorChecker Passport available from X-Rite; Grand Rapids, Mich., or equivalent), and a calibrated ruler (traceable to NIST, or equivalent) are laid horizontally flat on a matte black background inside a light box that provides stable uniform lighting evenly across the entire base of the light box. A suitable light box is the Sanoto MK50 (Sanoto, Guangdong, China), or equivalent, which provide an illumination of 5500 LUX at a color temperature of 5500K. A Digital Single-Lens Reflex (DSLR) camera with manual setting controls (e.g. a Nikon D40X available from Nikon Inc., Tokyo, Japan, or equivalent) is mounted directly above an opening in the top of the light box so that the entire article, color standard and ruler are visible within the camera's field of view.

Using a standard 18% gray card (e.g., Munsell 18% Reflectance (Gray) Neutral Patch/Kodak Gray Card R-27, available from X-Rite; Grand Rapids, MI, or equivalent), the camera's white balance is custom set for the lighting conditions inside the light box. The camera's manual settings are set so that the image is properly exposed such that there is no signal clipping in any of the color channels. Suitable settings might be an aperture setting of f/11, an ISO setting of 400, and a shutter speed setting of ¹/₄₀₀ sec. At a focal length of 35 mm the camera is mounted approximately 14 inches above the article. The image is properly focused, captured, and saved as a JPEG file. The resulting image must contain the entire article, color target, and calibrated ruler at a minimum resolution of 15 pixels/mm.

Absorbent article samples are conditioned at 23° C.±2 C.° and 50%±2% relative humidity for 2 hours prior to testing. Place a sample article flat, with the top sheet of the product facing upward. Position the tip of a mechanical pipette about 1 cm above the center (longitudinal and lateral midpoint) of the article's absorbent core, and accurately pipette 1.00 mL±0.05 mL of AMF onto the surface. The fluid is dispensed without splashing, within a period of 2 seconds. After the fluid has been acquired (no pool of fluid left on the surface), wait 2 minutes. In like fashion, a second and third dose of AMF are applied to the test sample. Carefully transfer the article into the light box, and place it flat onto the matte surface beneath the camera along with the ruler and color standard. The photographic image of the AMF dosed article is captured 2 minutes after the third AMF dose.

To analyze the image it is first transferred to a computer running an image analysis software (a suitable software is MATLAB, available from The Mathworks, Inc, Natick, MA, or equivalent).

The image is color calibrated using the true tristimulus XYZ color space values provided by the manufacturer for each of the 24 color chips in the color target. If target values are given in L*a*b* they are converted to XYZ according to the standard equations. The values are identified as Xtruel 24, Ytruel . . . 2a, and Z huel 24. Using the image analysis software the mean red, green, and blue (RGB) values of each of the 24 color chips in the image are measured using a square region of interest that covers approximately 75% of the interior area of each individual color chips. These values are identified as $R_{1 \ldots 24}$, $G_{1 \ldots 24}$, and $B_{1 \ldots 24}$. A system of 24 equations, using the $X_{true}$ and associated RGB values for each color tile, is set up according to the following example:

$$X_{true1}=\alpha_1+\alpha_2 R_1+\alpha_3 G_1+\alpha_4 B_1+\alpha_5 R_1^2+\alpha_6 R_1 G_1+ \alpha_7 G_1^2+\alpha_8 R_1 B_1+\alpha_9 G_1 B_1+\alpha_{10} B_1^2$$

$$X_{true24}=\alpha_1+\alpha_2 R_{24}+\alpha_3 G_{24}+\alpha_4 B_{24}+\alpha_5 R_{24}^2+\alpha_6 R_{24} G_{24}+ \alpha_7 G_{24}^2+\alpha_8 R_{24} B_{24} \alpha_9 G_{24} B_{24} \alpha_{10} B_{24}^2$$

A second system of 24 equations, using the $Y_{true}$ and associated RGB values for each color tile, is set up according to the following example:

$$Y_{true1}=\beta_1+\beta_2 R_1+\beta_3 G_1+\beta_4 B_1+\beta_5 R_1^2+\beta_6 R_1 G_1+\beta_7 G_1^2+ \beta_8 R_1 B_1+\beta_9 G_1 B_1+\beta_{10} B_1^2$$

$$Y_{true24}=\beta_1+\beta_2 R_{24}+\beta_3 G_{24}+\beta_4 B_{24}+\beta_5 R_{24}^2+\beta_6 R_{24} G_{24}+ \beta_7 G_{24}^2+\beta_8 R_{24} B_{24}+\beta_9 G_{24} B_{24}+\beta_{10} B_{24}^2$$

A third system of 24 equations, using the $Z_{true}$ and associated RGB values for each color tile, is set up according to the following example:

$$Z_{true1}=\gamma_1+\gamma_2 R_1+\gamma_3 G_1+\gamma_4 B_1+\gamma_5 R_1^2+\gamma_6 R_1 G_1+\gamma_7 G_1^2+ \gamma_8 R_1 B_1+\gamma_9 G_1 B_1+\gamma_{10} B_1^2$$

$$Z_{true24}=\gamma_1+\gamma_2 R_{24}+\gamma_3 G_{24}+\gamma_4 B_{24}+\gamma_5 R_{24}^2+\gamma_6 R_{24} G_{24}+ \gamma_7 G_{24}^2+\gamma_8 R_{24} B_{24}+\gamma_9 G_{24} B_{24}+\gamma_{10} B_{24}^2$$

Using the 24 $X_{true}$ equations, each of the ten α coefficients are solved for using the standard equation y=Ax, where y are the $X_{true}$, $Y_{true}$, and $Z_{true}$ vectors, A is the list of the measured RGB intensities, and x is a vector of the unknown alpha (α), beta (β), or gamma (γ) coefficients to be estimated.

For example, to solve for the a's in the transform that converts the RGB colors into colorimetric X tristimulus value, the arrays are as follows:

$$\hat{x} = \begin{bmatrix} \alpha_1 \\ \vdots \\ \alpha_{10} \end{bmatrix}$$

$$A = \begin{bmatrix} 1 & R_1 & G_1 & B_1 & R_1^2 & \cdots & B_1^2 \\ \vdots & \vdots & \vdots & \vdots & \vdots & \ddots & \vdots \\ 1 & R_{24} & G_{24} & B_{24} & R_{24}^2 & \cdots & B_{24}^2 \end{bmatrix}$$

$$y = \begin{bmatrix} X_{true1} \\ \vdots \\ X_{true24} \end{bmatrix}$$

The solution of the normal equations for x provides the least squares solution for the ten α coefficients according to the following equation:

$$\hat{x}=(A^T A)^{-1} A^T y$$

This procedure is repeated using the 24 $Y_{true}$ equations to solve for the ten β coefficients, and the 24 $Z_{true}$ equations to solve for the ten γ coefficients.

These coefficients are then plugged back into the original equations to provide three transform equations one each for X, Y, and Z, by which the RGB values for each individual pixel in the image are transformed into calibrated XYZ values. For example, the RGB transform equation for X using the 10 a coefficients is as follows:

$$X = \alpha_1 + \alpha_2 R + \alpha_3 G + \alpha_4 B + \alpha_5 R^2 + \alpha_6 RG + \alpha_7 G^2 + \alpha_8 RB + \alpha_9 GB + \alpha_{10} B^2$$

The XYZ values are then converted into CIE 1976 L*a*b* values as defined in CIE 15:2004 section 8.2.1.1 using D65 reference white.

The image resolution is calibrated using the calibrated distance scale in the image to determine the number of pixels per millimeter.

Separate images are generated for each of the individual L*, a*, and b* channels. The Chroma image is calculated using the following formula:

$$\text{Chroma} = \sqrt{(a^*)^2 + (b^*)^2}$$

Where a* and b* are the individual colorimetric images. The Chroma image is analyzed by manually drawing the region of interest (ROI) boundary around the visibly discernable perimeter of the entire AMF stain. The area of the ROI is calculated and reported as the Overall Stain Area to the nearest 0.1 mm² and the mean Chroma value within the ROI is calculated and recorded to the nearest 0.1 units.

The same ROI is analyzed for the a* image alone, and the mean a* value within the ROI is calculated and recorded to the nearest 0.1 units.

A minimum bounding rectangle is drawn around the ROI. This is the smallest rectangle that can be drawn within which all of the points of the ROI lie. The edges of the rectangle are parallel and perpendicular to the longitudinal and lateral axis of the absorbent article, such that the ROI height (H) is defined as the height of the bounding rectangle along the longitudinal axis of the article, and the ROI width (W) is defined as the width of the bounding rectangle along the lateral axis of the article. Both H and W are recorded to the nearest 0.1 mm.

The Chroma image is threshold at a value of 24 to generate a binary image. In the binary image the regions with a Chroma value greater than 24 appear as black, with a Gray Level (GL) value of 255, and remaining area as white, with a GL value of 0. Using the image analysis program, analyze each of the discrete black regions. Measure and record the areas of the individual discrete black regions to the nearest 0.1 mm², including any regions along the edges of the image. Sum all of the recorded areas to obtain the total area and report this value as the Interfacial Fluid Area to the nearest 0.1 mm².

The Topsheet Stain Area is measured by analyzing the AMF stained topsheet layer of the absorbent article sample. The article is set aside for approximately 30 min. after the AMF loading procedure, allowing the fluid on the article surface to fully dry. The entire topsheet layer of the article is carefully separated from the underlying layers and placed flat on a white background. The corners and edges of the topsheet are taped down such that its original longitudinal and lateral extension is maintained. A photographic image of the topsheet layer is collected, calibrated, and Chroma image generated according to the previously described procedures. The Chroma image is thresheld at a value which separates the regions containing dried AMF stain from the unstained regions on the topsheet to generate a binary image. In the binary image the regions with a Chroma value greater than the threshold value appear as black, with a Gray Level (GL) value of 255, and remaining area as white, with a GL value of 0. Using the image analysis program, analyze each of the discrete black regions. Measure and record the areas of the individual discrete black regions to the nearest 0.1 mm², including any regions along the edges of the image. Sum all of the recorded areas to obtain the total area and report this value as the Topsheet Stain Area to the nearest 0.1 mm².

This entire procedure is repeated on five substantially similar replicate articles. The reported value is the average of the five individual recorded measurements for Overall Stain Area to the nearest 0.1 mm², mean Chroma and a* to the nearest 0.1 units, H and W to the nearest 0.1 mm, Interfacial Fluid Area to the nearest 0.1 mm², and Topsheet Stain Area to the nearest 0.1 mm².

Composition Pattern Analysis

To determine the presence of a composition pattern (e.g. patterned surfactant) on the outermost body facing layer (i.e. topsheet) of an absorbent article, the layer is excised from the absorbent article and placed on the surface of colored water causing any composition pattern to exhibit the color of the water. If a composition pattern is observed, a photographic image is captured and further analysis is performed to measure the width and spacing of the discrete objects making up the composition pattern using image analysis. Test specimens are conditioned at 23° C.±2 C.° and 50%±2% relative humidity for 2 hours prior to testing and all testing is performed under these same environmental conditions.

A fresh absorbent article, within 6 months of the date of production, is obtained. The absorbent article is removed from its wrapper, if present, and a mark is made on the topsheet 3 mm inboard from each longitudinal end along the longitudinal axis. The distance between the two marks is measured and recorded as the gage length to the nearest 1 mm. To obtain a test specimen, the entire topsheet is excised from the article, using care to not impart any contamination or distortion to the layer during the process. A cryogenic spray (such as Quick-Freeze, Miller-Stephenson Company, Danbury, CT) may be used to remove the test specimen from the underlying layers if necessary. A test liquid is prepared by adding 0.05 wt % methylene blue dye (available from VWR International), or equivalent, to deionized water. The test specimen is exposed to the colored test liquid as follows.

A shallow dish is obtained that is large enough to allow the entire test specimen to lie horizontally flat inside. A total of 6 rectangular bars are obtained that are approximately 3 mm thick, 25 mm wide, and with a length equivalent to the width (lateral edge to lateral edge) of the test specimen at the gage marks. The bars are made of stainless steel (or equivalent) and heavy enough to sufficiently hold the test specimen in place. The test specimen is attached to two of the bars. Two bars are used as risers in the dish of liquid and the other two bars are used as risers in the light box.

The test specimen is placed on a horizontally flat surface with the garment side facing up. Using double sided tape that is about 3 mm wide, secure the test specimen to the bottom surface of two bars immediately outboard of the two gage marks. The distance between the test specimen bars is adjusted such that the distance between them is equal to the gage length. During subsequent handling of the test specimen, use care at all times to avoid twisting or stretching the test specimen beyond the gage length. One riser is placed at each end of the shallow dish such that the distance between them is equal to the gage length. The dish is filled with the colored test liquid to a depth equal to the height of the risers. The test specimen is transferred to the dish of colored test liquid and the bars placed onto the risers in the dish such that the body facing surface of the test specimen makes contact with the surface of the colored test liquid. If the test specimen has a composition pattern present it will become notably colored (e.g. blue) within 10 seconds due to wetting by the colored test liquid, and the test proceeds. If a composition pattern is not observed on the specimen the test is discontinued. After 10 seconds, if a composition pattern is observed, the test specimen is transferred (still attached to two bars) from the colored liquid to a sheet of blotting paper (e.g. Whatman grade 1, available from VWR International) that is the same size or larger than the test specimen. The body facing surface of the test specimen is allowed to make contact with the blotting paper for no more than 3 seconds to remove any droplets of test liquid from the back surface.

Without undue delay the test specimen is transferred into a light box that provides stable uniform lighting evenly across the entire base of the light box. A suitable light box is the Sanoto MK50 (Sanoto, Guangdong, China), or equivalent, which provides an illumination of 5500 lux at a color temperature of 5500K. The illumination and color temperature are verified using a light meter prior to capturing images inside the light box to ensure the lighting conditions are consistent between each image obtained. A suitable light meter is the CL-70F CRI Illuminance Meter available from Konica Minolta, or equivalent. Two riser bars are placed on a matte white surface inside the bottom of the light box such that the distance between them is equal to the gage length. The specimen bars are placed onto the risers, thereby suspending the specimen horizontally flat over the matte white surface.

A digital single-lens reflex (DSLR) camera with manual setting controls (e.g. a Nikon D40X available from Nikon Inc., Tokyo, Japan, or equivalent) is mounted directly above an opening in the top of the light box so that the entire test specimen is visible within the camera's field of view.

Using a standard 18% gray card (e.g., Kodak Gray Card R-27 with a Munsell 18% Reflectance (Gray) Neutral Patch, available from X-Rite; Grand Rapids, MI, or equivalent) the camera's white balance is custom set for the lighting conditions inside the light box. The camera's manual settings are set so that the image is properly exposed such that there is no signal clipping due to saturation in any of the color channels. Suitable settings might be an aperture setting of f/11, an ISO setting of 400, a shutter speed setting of 1/400 sec., and an approximate focal length of 35 mm. The camera is mounted approximately 14 inches directly above the specimen. The image is properly focused, captured, and saved as a 24 bit (8 bits per channel) RGB color JPEG file. The resulting image must contain the entire test specimen at a minimum resolution of 15 pixels/mm A photographic image of the entire test specimen is captured. The test specimen is removed from the light box. A distance scale (certified by NIST) is placed horizontally flat on top of the risers inside of the light box, and a calibration image is captured with the same camera settings and under the same lighting conditions as those used for the test specimen image.

Pattern Width Measurements:

Pattern images are spatially calibrated and analyzed using image analysis software (a suitable software is MATLAB, available from The Mathworks, Inc, Natick, MA, or equivalent). The calibration image is opened in the image analysis program and a linear distance calibration is performed using the distance scale captured in the calibration image. The test specimen image is opened in the image analysis program and the distance scale is set using the distance calibration to determine the number of pixels per millimeter. The RGB color pattern image is then converted to an 8 bit grayscale according to the following weighted sum of the R, G, and B components, where the gray level is rounded to the nearest integer value.

$$\text{Gray Level} = 0.2989 \times R + 0.5870 \times G + 0.1140 \times B$$

A 5×5 pixel median filter is applied to the image to remove noise, followed by a 5×5 pixel mean filter to smooth the image. The 8-bit grayscale image is then converted to a binary image by thresholding using Otsu's method, which calculates the threshold level that minimizes the weighted intra-class variance between foreground and background pixels. The discrete objects corresponding to the patterned surfactant in the binary image are identified with foreground pixels, and are assigned a value of 1 (one) while background pixels are assigned a value of 0 (zero). The individual objects in the binary image may contain bridging pixels that connect objects not apparently intended to be connected in the pattern. The foreground pattern objects are eroded enough times to separate patterned objects intended to be discrete in the pattern using a 3×3 square structuring element. This erosion operation removes any foreground pixel that is touching (an 8-connected neighbor to every pixel that touches one of their edges or corners) a background pixel, thereby removing a layer of pixels around the periphery of the patterned object. Using a 3×3 square structuring element, a dilation operation is then performed an equivalent number of times to restore the patterned objects to their original dimensions. This dilation operation converts any background pixel that is touching (8-connected neighbor) a foreground pixel into a foreground pixel, thereby adding a layer of pixels around the periphery of the patterned object. Holes within the patterned objects not apparently intended to be part of the pattern are closed by performing dilation operations a sufficient number of times to close holes within objects, followed by an equivalent number of iterations of erosion operations to restore the original dimensions of the object.

A connected components (8-connected neighbor) operation is utilized to identify all of the individual patterned objects. This connected components algorithm is executed on the binary image, which groups, or clusters, together the foreground pixels that are 8-connected (touching one of their edges or corners) to neighboring foreground pixels. Any remaining foreground pixel clusters that are not part of the regular pattern are removed or excluded from further analysis. The centroid of each patterned object is identified and its (x,y) coordinate location recorded.

A Euclidian distance map (EDM) of the patterned objects in the binary image is generated. An EDM is a transformed image in which each foreground pixel in the binary image is replaced with a value equal to that pixel's Euclidian distance from the nearest background pixel. The medial axis or skeleton of the foreground patterned objects in the binary image are identified using a skeletonization or thinning algorithm, followed by a pruning operation to remove small branches or spurs from the principal object skeleton. The skeleton image mask is multiplied by the distance map to isolate the distances to the patterned object boundary along the skeleton. The distance values along the skeleton are multiplied by two to obtain the width across the patterned object. The arithmetic mean distance value for all of the patterned objects within the pattern image is calculated and reported as the pattern width to the nearest 0.1 mm Pattern Spacing Measurements:

Using the recorded location of each patterned object's centroid, the Euclidian distance from each patterned object's centroid to all of the other patterned object centroids is calculated. For each patterned object, the shortest distance is identified and recorded as the nearest neighbor distance. Any spurious distance values that are not representative of the patterned objects within the pattern are excluded. The arithmetic mean nearest neighbor distance value for all of the patterned objects within the pattern image is calculated and reported as the pattern spacing distance to the nearest 0.1 mm Target Zone Test Method The Target Zone Test Method is used to determine the target zone length index value and the transverse width of the target zone at multiple characteristic points.

A two-dimensional shape, defined by the projection of a planar absorbent article perpendicular to both its longitudinal and transverse axes, is captured and is hereafter referred to as the article projection. The article projection retains the same longitudinal and transverse axes of the article itself. The centroid of the article projection is calculated, and the position of the centroid along the longitudinal axis of the article projection is defined as the article centroid point. A line extending through the article centroid point and parallel to the transverse axis is used to partition the article projection into two sub-shapes, a first article projection and a second article projection. The centroids of the first article projection and second article projection are calculated and defined as the first centroid and second centroid, respectively. The position of the first centroid along the longitudinal axis of the article projection is defined as the first article centroid point. The position of the second centroid along the longitudinal axis of the article projection is defined as the second article centroid point.

Lines extending through the first and second centroid points parallel to the transverse axis of the article projection delineate the front and rear boundaries of the target zone. The length of the target zone along the longitudinal axis is calculated and reported to the nearest 0.1 mm.

The target zone length index value is calculated by dividing the length of the target zone by the total length of the core projection along the longitudinal axis and is a dimensionless ratio reported to the nearest 0.01.

The transverse width of the article projection is measured at the front centroid point and rear centroid point and each is reported to the nearest 0.1 mm. The transverse width of the article projection is measured at the narrowest point within the target zone and reported to the nearest 0.1 mm.

All measures are performed on five substantially similar absorbent cores and reported as the arithmetic mean of the five values.

Contact Angle Method

Contact angles on substrates are determined using ASTM D7490-13 modified with the specifics as describe herein, using a goniometer and appropriate image analysis software (a suitable instrument is the FTA200, First Ten Angstroms, Portsmouth, VA, or equivalent) fitted with a 1 mL capacity, gas tight syringe with a No. 27 blunt tipped stainless steel needle. Two test fluids are used: Type II reagent water (distilled) in accordance with ASTM Specification D1193-99 and 99+% purity diiodomethane (both available from Sigma Aldrich, St. Louis, MO). All testing is to be performed at about 23° C.±2 C.° and a relative humidity of about 50%±2%.

A 50 mm by 50 mm nonwoven substrate to be tested is removed from the article taking care to not touch the region of interest or otherwise contaminate the surface during harvesting or subsequent analysis. Condition the samples at about 23° C.±2 C.° and a relative humidity of about 50%±2% for 2 hours prior to testing.

Set up the goniometer on a vibration-isolation table and level the stage according to the manufacturer's instructions. The video capture device must have an acquisition speed capable of capturing at least 10-20 images from the time the drop hits the surface of the specimen to the time it cannot be resolved from the specimen's surface. A capture rate of 900 images/sec is typical. Depending on the hydrophobicity/hydrophilicity of the specimen, the drop may or may not rapidly wet the surface of the nonwoven sample. In the case of slow acquisition, the images should be acquired until 2% of the volume of the drop is absorbed into the specimen. If the acquisition is extremely fast, the first resolved image should be used if the second image shows more than 2% volume loss.

Place the specimen on the goniometer's stage and adjust the hypodermic needle to the distance from the surface recommended by the instrument's manufacturer (typically 3 mm). If necessary adjust the position of the specimen to place the target site under the needle tip. Focus the video device such that a sharp image of the drop on the surface of the specimen can be captured. Start the image acquisition. Deposit a 5 µL±0.1 µL drop onto the specimen. If there is visible distortion of the drop shape due to movement, repeat at a different, but equivalent, target location. Make two angle measurements on the drop (one on each drop edge) from the image at which there is a 2% drop volume loss. If the contact angles on two edges are different by more than 4°, the values should be excluded and the test repeated at an equivalent location on the specimen. Identify five additional equivalent sites on the specimen and repeat for a total of 6 measurements (12 angles). Calculate the arithmetic mean for this side of the specimen and report to the nearest 0.01°. In like fashion, measure the contact angle on the opposite side of the specimen for 6 drops (12 angles) and report separately to the nearest 0.01°.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising a longitudinal centerline and a lateral centerline, a machine direction (MD) generally oriented parallel to the longitudinal centerline and a cross direction (CD) generally oriented parallel to the lateral centerline, the absorbent article further comprising:
  a topsheet having a first surface and a second surface, the topsheet comprising a nonwoven material made up of a plurality of filaments or fibers;
  a backsheet;
  an absorbent core disposed between the topsheet and the backsheet;
  a plurality of composition elements disposed on the topsheet, wherein each of the composition elements comprise an element width and an element spacing between adjacent elements, wherein a ratio of element spacing to element width is between about 0.5 to about 8, as measured by the Composition Pattern Analysis;
  wherein the composition of each of the plurality of composition elements is more hydrophilic than the filaments or fibers of the nonwoven web.

2. The absorbent article of claim 1, wherein the elements comprise stripes oriented in the CD.

3. The absorbent article of claim 1, wherein the elements comprise stripes oriented in the MD.

4. The absorbent article of claim 1, wherein the element width is between about 1.4 mm to about 5 mm, as measured by Composition Pattern Analysis.

5. The absorbent article of claim 1, wherein the element spacing is between about 1.6 mm to about 6 mm, as measured by the Composition Pattern Analysis.

6. The absorbent article of claim 1, further comprising a target zone and a pair of outer zones which flank the target zone, wherein the plurality of composition elements are applied at a first ratio of element spacing to element width in the target zone and at a second ratio of element spacing to element width in the outer zone, wherein the first ratio and the second ratio are different, and wherein the first ratio and the second ratio are determined via the Composition Pattern Analysis.

7. The absorbent article of claim 6, wherein the outer zones are disposed on a first end and a second end of the absorbent article, and wherein the target zone is disposed therebetween.

8. The absorbent article of claim 6, wherein one of the outer zones is disposed along a first longitudinal side edge and another of the outer zones is disposed along a second longitudinal side edge, and wherein the target zone is disposed therebetween.

9. The absorbent article of claim 6, wherein the first ratio is higher than the second ratio.

10. An absorbent article comprising a longitudinal centerline and a lateral centerline, a machine direction (MD) generally oriented parallel to the longitudinal centerline and a cross direction (CD) generally oriented parallel to the lateral centerline, the absorbent article further comprising:
  a topsheet having a first surface and a second surface, the topsheet comprising a nonwoven material made up of a plurality of filaments or fibers;
  a backsheet
  an absorbent core disposed between the topsheet and the backsheet
  a plurality of composition elements disposed on the topsheet, wherein each of the composition elements comprise an element width and an element spacing between adjacent elements, wherein a ratio of element spacing to element width is between about 0.5 to about 8, as measured by the Composition Pattern Analysis;
  wherein the absorbent article further comprises a target zone and a pair of outer zones which flank the target zone, wherein the plurality of composition elements are applied at a first ratio of element spacing to element width in the target zone and at a second ratio of element spacing to element width in the outer zone, wherein the first ratio and the second ratio are different, and wherein the first ratio and the second ratio are determined via the Composition Pattern Analysis; wherein the first ratio is lower than the second ratio.

11. An array of absorbent articles comprising a first absorbent article and a second absorbent article, each of the first absorbent article and the second absorbent article comprising a topsheet, a backsheet, an absorbent core disposed between the topsheet and the backsheet, and a first plurality of composition elements applied to a first topsheet of the first absorbent article and a second plurality of composition elements applied to a second topsheet of the second absorbent article, wherein the first plurality of composition elements has a first ratio of composition element spacing to composition element width as measured by the Composition Pattern Analysis, and the second plurality of composition elements has a second ratio of composition element spacing to composition element width as measured by the Composition Pattern Analysis, and wherein the first ratio is different than the second ratio; wherein the first ratio is less than the second ratio.

12. The array of claim 11, wherein the first absorbent article comprises a feminine sanitary pad and the second absorbent article is not a feminine sanitary pad.

13. The array of claim 11, wherein the first ratio is greater than the second ratio.

14. The array of claim 11, wherein the first absorbent article is a feminine sanitary pad having a first size and the second absorbent article is a feminine sanitary pad having a second size that is different than the first size.

15. The array of claim 11, wherein the first absorbent article further comprises a first target zone and a pair of outer zones flanking the first target zone, and wherein the first ratio is with respect to the first plurality of composition elements in the first target zone.

16. The array of claim 15, wherein the outer zones are disposed on a first end and a second end of the absorbent article, and wherein the first target zone is disposed therebetween.

17. The array of claim 15, wherein one of the outer zones is disposed along a first longitudinal side edge and another of the outer zones is disposed along a second longitudinal side edge, and wherein the first target zone is disposed therebetween.

18. The array of claim 15, wherein the second absorbent article further comprises a second target zone and a pair of outer zones flanking the second target zone, and wherein the second ratio is with respect to the second plurality of composition elements in the second target zone.

19. An absorbent article comprising a longitudinal centerline and a lateral centerline, a machine direction (MD) generally oriented parallel to the longitudinal centerline and a cross direction (CD) generally oriented parallel to the lateral centerline, the absorbent article further comprising:
  a topsheet having a first surface and a second surface, the topsheet comprising a nonwoven material made up of a plurality of filaments or fibers;
  a backsheet;
  an absorbent core disposed between the topsheet and the backsheet;
  a plurality of composition elements disposed on the topsheet, wherein each of the composition elements comprise an element width and an element spacing between adjacent elements, wherein a ratio of element spacing to element width is between about 0.5 to about 8, as measured by the Composition Pattern Analysis; wherein the composition elements comprise stripes oriented in the CD.

* * * * *